United States Patent
Ishii et al.

(10) Patent No.: US 7,459,586 B2
(45) Date of Patent: Dec. 2, 2008

(54) OPTICALLY ACTIVE 1-ARYL-2-FLUORO-SUBSTITUTED ETHYLAMINE AND METHOD FOR PRODUCING SAME

(75) Inventors: Akihiro Ishii, Saitama (JP); Masatomi Kanai, Saitama (JP); Yokusu Kuriyama, Saitama (JP); Manabu Yasumoto, Saitama (JP); Kenjin Inomiya, Saitama (JP); Takashi Ootsuka, Saitama (JP); Katsuhide Suto, Saitama (JP); Koji Ueda, Saitama (JP)

(73) Assignee: Central Glass Company Limited, Ube-shi (JP)

( * ) Notice: Subject to any disclaimer, the term of this patent is extended or adjusted under 35 U.S.C. 154(b) by 95 days.

(21) Appl. No.: 10/591,669

(22) PCT Filed: Feb. 21, 2005

(86) PCT No.: PCT/JP2005/002740

§ 371 (c)(1),
(2), (4) Date: Sep. 1, 2006

(87) PCT Pub. No.: WO2005/085174

PCT Pub. Date: Sep. 15, 2005

(65) Prior Publication Data

US 2007/0191639 A1 Aug. 16, 2007

(30) Foreign Application Priority Data

Mar. 5, 2004 (JP) ............................. 2004-062735

(51) Int. Cl.
C07C 209/62 (2006.01)
C07C 211/00 (2006.01)
C07C 251/00 (2006.01)

(52) U.S. Cl. ...................... 564/386; 564/271; 564/272; 564/366

(58) Field of Classification Search ........................ None
See application file for complete search history.

(56) References Cited

U.S. PATENT DOCUMENTS

2002/0119992 A1 8/2002 Selnick et al.

FOREIGN PATENT DOCUMENTS

WO WO 02/50056 A1 6/2002

OTHER PUBLICATIONS

European Search Report dated May 7, 2007 (Three (3) pages).
Kanai M. et al., "Highly Regioselective Hydrogenolysis of Bis(alpha-methylbenzyl)amine Derivatives Affected by the Trifluoromethyl Substituent on the Aromatic Ring", vol. 5, No. 7, Apr. 3, 2003, XP-002430269, (pp. 1007-1010).
Gosselin F. et al., "Unprecedented Catalytic Asymmetric Reduction of N-H Imines", vol. 7, No. 2, Jan. 20, 2005, XP-002430270, (pp. 355-358).
International Search Report dated May 31, 2005 with an English translation of the pertinent portions (Five (5) pages).
Torok, B. et al., "Synthesis of Chiral Trifluoromethylated Amines by Palladium-Catalyzed Diastereoselective Hydrogenation-Hydrogenolysis Approach", Advanced Synthesis & Catalysis, 2003 vol. 345, No. 1+2, (pp. 165-168).
Pirkle, W.H. et al., "Design of Chiral Derivatizing Agents for the Chromatographic Resolution of Optical Isomers. Asymmetric Synthesis of Some Chiral Fluoroalkylated Amines", Journal of Organic Chemistry, 1977 vol. 42, No. 14, (pp. 2436-2439).
Kato, K. et al., "Enzymatic resolution of 2,2,2-trifluoro-1-arylethylamine derivatives by Pseudomonas fluorescens lipase in organic solvents", Journal of Molecular Catalysis B: Enzymatic, 2004, vol. 30, (pp. 61-68).
Blaauw, R. H. et al., "Intramolecular Photochemical Dioxenone-Alkene [2+2] Cycloadditions as an Approach to the Bicyclo[2.1.1]hexane Moiety of Solanoeclepin A", Journal of Organic Chemistry, 2001, vol. 66, (pp. 233-242).
Prakash, G. K. S. et al., "Facile preparation of di- and monofluoromethyl ketones from trifluoromethyl ketones via fluorinated enol silyl ethers", Journal of Fluorine Chemistry, 2001, vol. 112, (pp. 357-362).

*Primary Examiner*—Brian J Davis
(74) *Attorney, Agent, or Firm*—Crowell & Moring LLP

(57) ABSTRACT

The present invention relates to a method of producing an optically active 1-aryl-2-fluoro-substituted ethylamine compound of the formula [2] or a salt thereof by hydrogenolysis of an optically active secondary amine compound of the formula [1] or a salt thereof in the presence of a transition metal catalyst of Group VIII

[Chem. 59]

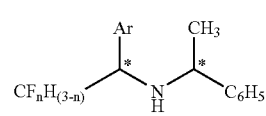

[1]

[where Ar represents an aryl group; n represents an integer of 1 or 2; and * represents an asymmetric carbon]

[Chem. 60]

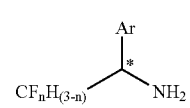

[2]

[where Ar represents an aryl group; n represents an integer of 1 or 2; and * represents an asymmetric carbon].

21 Claims, No Drawings

OPTICALLY ACTIVE 1-ARYL-2-FLUORO-SUBSTITUTED ETHYLAMINE AND METHOD FOR PRODUCING SAME

TECHNICAL FIELD

The present invention relates to optically active 1-aryl-2-fluoro-substituted ethylamines useful as important intermediates for medicines and agricultural chemicals and their production method.

BACKGROUND OF THE INVENTION

Optically active 1-aryl-2-fluoro-substituted ethylamines, which are the subject of the present invention, are useful as important intermediates for medicines and agricultural chemicals. For example, a thrombin inhibitor having a racemic 1-aryl-2-fluoro-substituted ethylamine structure in its partial skeleton are being under development (Patent Publication 1). The optically active 1-aryl-2-fluoro-substituted ethylamines and their production method have become particularly important with the establishment of the concept of a chiral drug, by which, when there exist optical isomers, drug developments proceed with using either one of the optical isomers required.

The optically active 1-aryl-2-fluoro-substituted ethylamines of the present invention are novel materials, so that there are no reports made on their production method.

As prior art relevant to the present invention, there are reports about: (1) a method of synthesizing a para-methoxyphenyl (PMP) protected racemic 1-aryl-2-fluorosubstituted ethylamine by reaction of N-(4-methoxy phenyl)-N-2,2-difluoroethylidene)amine and an aryl lithium compound (Patent Publication 1); (2) a method of synthesizing an acetyl protected racemic 1-aryl-2-fluoro-substituted ethylamine by desililation and fluorination of an alkenyl trimethylsilane (Non-patent Publication 1) and (3) a method of synthesizing a hydrochloride of optically active 1-phenyl-2,2,2-trifluoroethylamine of the formula [18] by hydrogenolysis of a hydrochloride of optically active secondary amine of the formula [17] in the presence of a palladium catalyst

[Chem. 1]

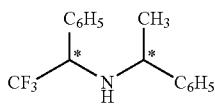

[where * represents an asymmetric carbon]

[Chem. 2]

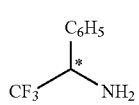

[where * represents an asymmetric carbon].

Patent Publication 1: PCT 02/50056
Non-patent Publication 1: J. Org. Chem., (U.K.), 2001, pp. 233-234
Non-patent Publication 2: J. Org. Chem., (U.S.), 1977, Vol. 42, No. 14, pp. 2436-2439

SUMMARY OF THE INVENTION

It is an object of the present invention to provide an industrial production method of optically active 1-aryl-2-fluoro-substituted ethylamines usable as important intermediates for medicines and agricultural chemicals. According to the present invention, there is provided a method (referred to as a "first method") of producing an optically active 1-aryl-2-fluoro-substituted ethylamine compound of the formula [2] or a salt thereof by hydrogenolysis of an optically active secondary amine compound of the formula [1] or a salt thereof in the presence of a transition metal catalyst of Group VIII

[Chem. 3]

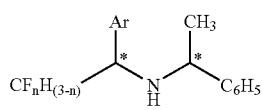

[where Ar represents an aryl group; n represents an integer of 1 or 2. and * represents an asymmetric carbon]

[Chem. 4]

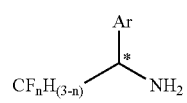

[where Ar represents an aryl group; n represents an integer of 1 or 2. and * represents an asymmetric carbon].

The first method may be a method (referred to as a "second method") of producing an optically active 1-aryl-2-fluoro-substituted ethylamine compound of the formula [4] or a salt thereof by hydrogenolysis of an optically active secondary amine compound of the formula [3] or a salt thereof in the presence of a palladium catalyst

[Chem. 5]

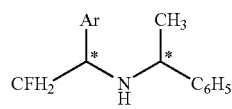

[where Ar represents an aryl group; and * represents an asymmetric carbon]

[Chem. 6]

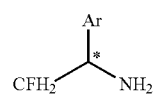

[where Ar represents an aryl group; and * represents an asymmetric carbon].

Further, the first method may be a method (referred to as a "third method") of producing an optically active 1-aryl-2-fluoro-substituted ethylamine compound of the formula [6] or a salt thereof by hydrogenolysis of an optically active secondary amine compound of the formula [5] or a salt thereof in the presence of a palladium catalyst

[Chem. 7]

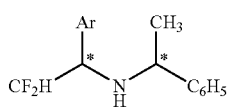

[5]

[where Ar represents an aryl group; and * represents an asymmetric carbon]

[Chem. 8]

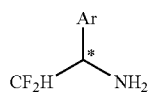

[6]

[where Ar represents an aryl group; and * represents an asymmetric carbon].

The optically active secondary amine of the formula [1] may be an optically active secondary amine obtained by a method (hereinafter referred to as a "fourth method") that includes the steps of: preparing an optically active imine of the formula [9] by dehydration condensation of a fluoro-substituted methyl aryl ketone of the formula [7] and an optically active 1-phenylethylamine of the formula [8] in the presence of an acid catalyst

[Chem. 9]

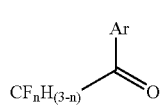

[7]

[where Ar represents an aryl group; and n represents an integer of 1 or 2]

[Chem. 10]

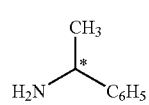

[8]

[where * represents an asymmetric carbon]

[Chem. 11]

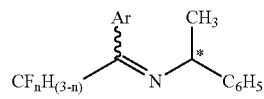

[9]

[where Ar represents an aryl group; n represents an integer of 1 or 2; * represents an asymmetric carbon; and the wavy line represents E configuration or Z configuration];

preparing an optically active secondary amine of the formula [10] in the form of a mixture of diastereomers by asymmetric reduction of the optically active imine

[Chem. 12]

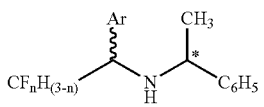

[10]

[where Ar represents an aryl group; n represents an integer of 1 or 2; * represents an asymmetric carbon; and the wavy line represents a mixture of diastereomers];

deriving a salt from the mixture of diastereomers of the optically active secondary amine; and purifying the salt by recrystallization.

The optically active secondary amine of the formula [3] may be an optically active secondary amine obtained by a method (hereinafter referred to as a "fifth method") that includes the steps of: preparing an optically active imine of the formula [12] by dehydration condensation of a fluoro-substituted methyl aryl ketone of the formula [11] and an optically active 1-phenylethylamine of the formula [8] in the presence of an acid catalyst

[Chem. 13]

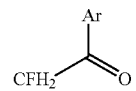

[11]

[where Ar represents an aryl group]

[Chem. 14]

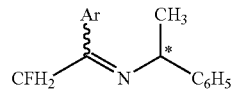

[12]

[where Ar represents an aryl group; * represents an asymmetric carbon; and the wavy line represents E configuration or Z configuration];

preparing an optically active secondary amine of the formula [13] in the form of a mixture of diastereomers by asymmetric reduction of the optically active imine with a hydride reducing agent

[Chem. 15]

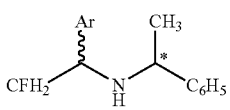

[where Ar represents an aryl group; * represents an asymmetric carbon; and the wavy line represents a mixture of diastereomers];

deriving a salt from the mixture of diastereomers of the optically active secondary amine; and purifying the salt by recrystallization.

The optically active secondary amine of the formula [5] may be an optically active secondary amine obtained by a method (hereinafter referred to as a "sixth method") that includes the steps of: preparing an optically active imine of the formula [15] by dehydration condensation of a fluoro-substituted methyl aryl ketone of the formula [14] and an optically active 1-phenylethylamine of the formula [8] in the presence of an acid catalyst

[Chem. 16]

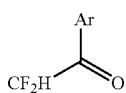

[where Ar represents an aryl group]

[Chem. 17]

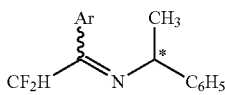

[where Ar represents an aryl group; * represents an asymmetric carbon; and the wavy line represents E configuration or Z configuration];

preparing an optically active secondary amine of the formula [16] in the form of a mixture of diastereomers by asymmetric reduction of the optically active imine with a hydride reducing agent

[Chem. 18]

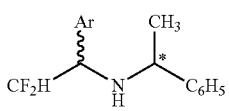

[where Ar represents an aryl group; * represents an asymmetric carbon; and the wavy line represents a mixture of diastereomers];

deriving a salt from the mixture of diastereomers of the optically active secondary amine; and purifying the salt by recrystallization.

DETAILED DESCRIPTION

The synthesis methods of Patent Publication 1 and Non-patent Publication 1 are strictly for the purpose of synthesizing racemic modifications and cannot be used to produce the optically active compounds of the present invention. Further, it is shown in Non-patent Publication 2 that the hydrogenolysis of a secondary amine proceeds with high regioselectivity when the amine has different substituents i.e. methyl and trifluoromethyl groups at α- and α'-positions as indicated in Scheme 1, so that the reaction mechanism of such highly regioselective hydrogenolysis is applicable to the production of optically active 1-phenyl-2,2,2-trifluoroethylamine.

Scheme 1

[Chem. 19]

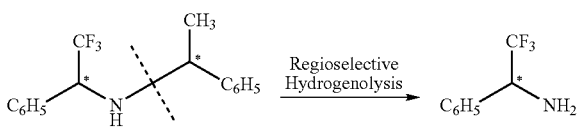

However, no report has been made on whether the hydrogenolysis of the secondary amine could proceed with high regioselectivity even when the amine alternatively has difluoromethyl or monofluoroethyl and methyl substituent groups.

It is also unclear whether the synthesis method of Non-patent Publication 2 could be applied to producing the optically active 1-aryl-2-fluoro-substituted ethylamines of the present invention industrially at high chemical and optical purity from the fluoro-substituted methyl aryl ketone of the formula [7] and the optically active 1-phenylethylamine of the formula [8]. There is no disclosure in Non-patent Publication 2 about the purification process for the optically active secondary amine of the formula [17], whereby the optically active secondary amine undergoes hydrogenolysis in the form of a mixture of diastereomers so that the optically active 1-phenyl-2,2,2-fluoroethylamine cannot be obtained at high optical purity. It is necessary to purify the reaction product to a high optical purity by optical resolution with the use of optically active tartaric acid. The synthesis method of Non-patent Publication 2 is thus not totally suitable for industrial use.

Against this backdrop, there is a strong demand to develop a method for producing an optically active 1-aryl-2-fluoro-substituted ethylamine industrially at high chemical purity and at high optical purity.

The present inventors have found, as a result of extensive researches, that the hydrogenolysis of the secondary amine proceeds with high regioselectivity even when the amine has difluoromethyl or monofluoroethyl and methyl substituent groups.

When the synthesis method of Non-patent Publication 2 is applied to the present invention especially by using the fluoro-substituted methyl aryl ketone (monofluoromethyl aryl ketone) of the formula [11] as a raw substrate material, the optically active imine of the formula [12] is given in the form of a mixture of E- and Z-configuration isomers. The asymmetric reduction of such an isomeric mixture results in the optically active secondary amine of the formula [13] being formed with low diastereo-selectivity. The optically active 1-aryl-2-fluoro-substituted ethylamine of the formula [4] cannot be thus obtained at high optical purity. This raises a need to establish a purification process for the reaction product. The present inventors have found, as a result of extensive researches on various purification processes, that the mixture of diastereomers of the optically active secondary amine of the formula [13] can be purified to a high diastereomer excess by deriving a salt therefrom and purifying the salt by recrystallization. The present inventors have further found that this purification process is also effective for purifying the mixture of diastereomers of the optically active secondary amine (difluoro compound) of the formula [16].

In the hydrogenolysis of the optically active secondary amine (monofluoro compound) of the formula [3], there arises a considerable amount of by-product impurity if the amine is present as a free base. It is estimated that the fluorine atom acts as a leaving group to form 2-arylethylamine with a linear rearranged carbon skeleton as a by-product via an aziridine intermediate. (See Scheme 2.)

Scheme 2

[Chem. 20]

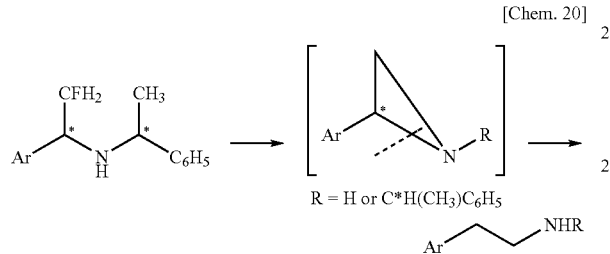

The present inventors have found, as a result of extensive researches on various hydrogenolysis conditions, that the optically active 1-aryl-2-fluoro-substituted ethylamine of the formula [4] can be obtained at high purity, with almost no side reaction, by directly subjecting the purified salt to a hydrogenolysis reaction or by subjecting the amine to a hydrogenolysis reaction after adding an acid to the free base. The present inventors have further found that these hydrogenolysis conditions are also effective for the hydrogenolysis of the optically active secondary amine (difluoro compound) of the formula [5].

In other words, the present inventors have found novel optically active 1-aryl-2-fluoro-substituted ethylamines, their effective production method as well as noble intermediate compounds obtained in the production method. The present invention is based on such findings.

The production method of the present invention is so high in reaction selectivity as to provide almost no hard-to-separate by-product impurities and is thus effective for industrially producing the optically active amines at high chemical and optical purity.

A target compound of the optically active 1-aryl-2-fluoro-substituted ethylamine of the present invention can be produced by e.g. a seventh method that combines the first method and the fourth method. Namely, the seventh method includes four steps: (1) dehydration condensation, (2) asymmetric reduction, (3) salt purification, and (4) hydrogenolysis. (See Scheme 3.)

Scheme 3

[Chem. 21]

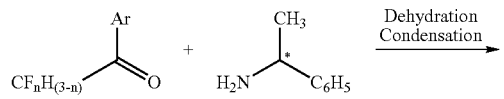

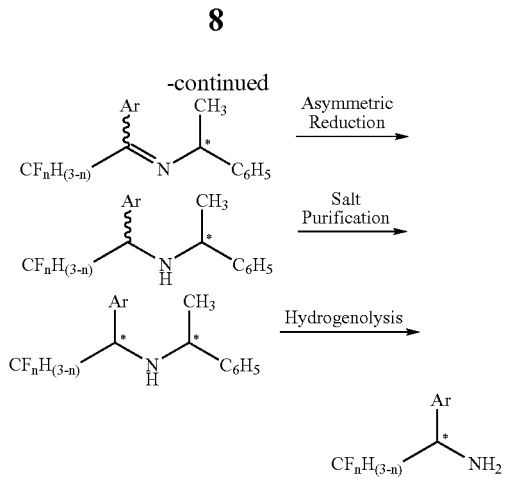

The first step: "dehydration condensation" will be now described below in detail. The dehydration condensation of the first step is conducted by subjecting the fluoro-substituted methyl aryl ketone of the formula [7] and the optically active 1-phenylethylamine of the formula [8] to dehydration condensation in the presence of the acid catalyst.

Examples of Ar of the fluoro-substituted methyl aryl ketone of the formula [7] include unsubstituted phenyl, phenyl substituted with C1-C4 lower alkyl, phenyl substituted with halogen (fluorine, chlorine, bromine), phenyl substituted with C1-C4 lower haloalkyl, phenyl substituted with C1-C4 lower alkoxy, phenyl substituted with C1-C4 lower haloalkoxy, phenyl substituted with C1-C4 lower alkylamino, phenyl substituted with C1-C4 lower alkylthio, phenyl substituted with any two or more of the above lower alkyl, halogen, lower haloalkyl, lower alkoxy, lower haloalkoxy, lower alkylamino and lower alkylthio substituents, unsubstituted naphtyl, naphtyl substituted with C1-C4 lower alkyl, naphtyl substituted with halogen (fluorine, chlorine, bromine), naphtyl substituted with C1-C4 lower haloalkyl, naphtyl substituted with C1-C4 lower alkoxy, naphtyl substituted with C1-C4 lower haloalkoxy, naphtyl substituted with C1-C4 lower alkylamino, naphtyl substituted with C1-C4 lower alkylthio, naphtyl substituted with any two or more of the above lower alkyl, halogen, lower haloalkyl, lower alkoxy, lower haloalkoxy, lower alkylamino and lower alkylthio substituents, unsubstituted oxygen-containing aromatic heterocycle, oxygen-containing aromatic heterocycle substituted with C1-C4 lower alkyl, oxygen-containing aromatic heterocycle substituted with halogen (fluorine, chlorine, bromine), oxygen-containing aromatic heterocycle substituted with C1-C4 lower haloalkyl, oxygen-containing aromatic heterocycle substituted with C1-C4 lower alkoxy, oxygen-containing aromatic heterocycle substituted with C1-C4 lower haloalkoxy, oxygen-containing aromatic heterocycle substituted with C1-C4 lower alkylamino, oxygen-containing aromatic heterocycle substituted with C1-C4 lower alkylthio, oxygen-containing aromatic heterocycle substituted with any two or more of the above lower alkyl, halogen, lower haloalkyl, lower alkoxy, lower haloalkoxy, lower alkylamino and lower alkylthio substituents, unsubstituted nitrogen-containing aromatic heterocycle, nitrogen-containing aromatic heterocycle substituted with C1-C4 lower alkyl, nitrogen-containing aromatic heterocycle substituted with halogen (fluorine, chlorine, bromine), nitrogen-containing aromatic heterocycle substituted with C1-C4 lower haloalkyl, nitrogen-containing aromatic heterocycle substituted with C1-C4 lower alkoxy, nitrogen-containing aromatic heterocycle substituted with C1-C4 lower haloalkoxy, nitrogen-containing aromatic heterocycle substituted with C1-C4 lower alkylamino, nitrogen-containing aromatic heterocycle substituted with C1-C4 lower alkylthio, nitrogen-containing aromatic heterocycle substituted with any two or more of the above lower alkyl, halogen, lower haloalkyl, lower alkoxy, lower haloalkoxy, lower alkylamino and lower alkylthio substituents, unsubstituted sulfur-containing aromatic heterocycle, sulfur-containing aromatic heterocycle substituted with C1-C4 lower alkyl, sulfur-containing aromatic heterocycle substituted with halogen (fluorine, chlorine, bromine), sulfur-containing aromatic heterocycle substituted with C1-C4 lower haloalkyl, sulfur-containing aromatic heterocycle substituted with C1-C4 lower alkoxy, sulfur-containing aromatic heterocycle substituted with C1-C4 lower haloalkoxy, sulfur-containing aromatic heterocycle substituted with C1-C4 lower alkylamino, sulfur-containing aromatic heterocycle substituted with C1-C4 lower alkylthio, and sulfur-containing aromatic heterocycle substituted with any two or more of the above lower alkyl, halogen, lower haloalkyl, lower alkoxy, lower haloalkoxy, lower alkylamino and lower alkylthio substituents. There are varieties of the fluoro-substituted methyl aryl ketone, some of which are novel, that can be produced using raw substrate materials of different aryl (Ar) groups with reference to J. Fluorine Chem., (Finland), 2001, Vol. 112, p. 357-362 etc.

As the absolute configuration at the asymmetric carbon atom of the optically active 1-phenylethylamine of the formula [8], both of R configuration and S configuration are possible. The isomers of these configurations are selectively used depending on the absolute configuration of the target optically active 1-aryl-2-fluoro-substituted ethylamine of the formula [2].

There is no particular restriction on the optical purity of the optically active 1-phenylethylamine of the formula [8], and it suffices that the optically active 1-phenylethylamine of the formula [8] has an enantiomeric excess (e. e.) of 95% or greater, generally preferably 97% e.e. or greater, more preferably 99% e.e. or greater.

There is no particular restriction on the amount of the optically active 1-phenylethylamine of the formula [8] used, and it suffices to use the optically active 1-phenylethylamine of the formula [8] in an amount of 0.8 mol or greater, generally preferably 0.9 to 10 mols, more preferably 1.0 to 5 mols, relative to 1 mol of the fluoro-substituted methyl aryl ketone of the formula [7].

As the acid catalyst, there can be used: organic acids such as formic acid, acetic acid, propionic acid, trifluoroacetic acid, methanesulfonic acid, trifluoromethanesulfonic acid, benzenesulfonic acid, para-toluenesulfonic acid (PTS), pyridinium paratoluene sulfonate (PPTS) and 10-camphorsulfonic acid; ion exchange resins such as Amberlyst H-15 and Dowex 50W-X8. and inorganic acids such as hydrochloric acid, hydrobromic acid, sulfuric acid, phosphoric acid, zinc chloride and titanium tetrachloride. Among them, pyridiniumparatoluene sulfonate (PPTS), sulfuric acid and zinc chloride are preferred. More preferred are pyridiniumparatoluene sulfonate (PPTS) and zinc chloride.

There is no particular restriction on the amount of the acid catalyst used, and it suffices to use the acid catalyst in an effective amount, generally preferably in an amount of 0.001 to 0.9 mol, more preferably 0.005 to 0.7 mol, relative to 1 mol of the fluoro-substituted methyl aryl ketone of the formula [7].

The dehydration-condensation reaction of the fluoro-substituted methyl aryl ketone and the optically active 1-phenylethylamine is preferably conducted while removing water that occurs as a by-product under acidic conditions. For example, the by-product water can be removed by using any reaction solvent immiscible with water, lower in specific gravity than water and capable of forming an azeotrope with water, together with a Dean-Stark tube, under reflux conditions, or by using a desiccant such as synthetic zeolite (trade name: Molecular Sieve), anhydrous phosphoric acid, anhydrous magnesium sulfate or anhydrous sodium sulfate.

As the reaction solvent, aromatic hydrocarbons such as benzene, toluene, ethylbenzene, xylene and mesitylene are preferred. More preferred are toluene and xylene. These reaction solvents can be used alone or in combination thereof.

There is no particular restriction on the amount of the reaction solvent used, and it suffice to use the reaction solvent in an amount of 0.01 L (liter) or greater, generally preferably 0.05 to 20 L, more preferably 0.1 to 10 L, relative to 1 mole of the fluoro-substituted methyl aryl ketone of the formula [7].

The temperature condition is generally 25 to 250° C., preferably 50 to 200° C., more preferably 75 to 150° C.

The reaction time is generally 0.1 to 72 hours, but it varies depending on the reaction substrate and conditions. It is thus preferable to trace the progress of the reaction by any analytical means such as gas chromatography, liquid chromatography or NMR, and then, determine as a reaction end point the time at which the raw substrate material has almost disappeared.

Although the post-treatment is not particularly limited, the optically active imine of the formula [9] is obtained as a crude product by performing a normal post-treatment operation after the termination of the dehydration-condensation reaction. In particular, the unreacted optically active 1-phenylethylamine can be selectively removed by washing the reaction-terminated liquid or organic phase containing the target optically active imine of the formula [9] with an ammonium chloride aqueous solution. Further, the optically active imine of the formula [9] can be obtained at high purity by subjecting the crude product to any purification operation such as activated carbon treatment, distillation, recrystallization and/or column chromatography as needed. The reaction-terminated liquid may be used in the subsequent asymmetric reduction step without being subjected to any post-treatment operation. Herein, the optically active imine is in the form of a mixture of E and Z configuration isomers due to the geometrical isomerism of the double bond, and the formation ratio between these configuration isomers varies depending on the reaction substrate and conditions. Both of the E and Z configuration isomers are useable as a raw substrate material in the subsequent asymmetric reduction step.

Next, the second step: "asymmetric reduction" will be described below in detail. The asymmetric reduction of the second step is conducted by subjecting the optically active imine of the formula [9] to asymmetric hydrogenation in the presence of the transition metal catalyst of Group VIII (Groups 8 to 10) or to asymmetric reduction with the hydride reducing agent. (Refer to the fifth or sixth method.)

As the absolute configuration at the newly-introduced asymmetric carbon of the diastereomeric mixture of the optically active secondary amine of the formula [10], both of R and S configurations are possible. The ratio between these configurations varies depending on the reaction substrate and conditions. Accordingly, there exist any of R—R configuration, S—R configuration, R—S configuration and S—S configuration isomers depending on the combination of the absolute configurations at two asymmetric carbons. (Herein, the character before the hyphen identifies the absolute configuration at the newly-introduced asymmetric carbon, and the character after the hyphen identifies the absolute configuration at the asymmetric carbon derived from the optically active 1-phenylethylamine of the formula [8].)

The process of asymmetric hydrogenation of the optically active imine in the presence of the transition metal catalyst of Group VIII will be now explained in detail.

Specific examples of the transition metal catalyst of Group VIII include: platinum catalysts such as platinum oxide, platinum/active carbon and platinum black; nickel catalysts such as reduced nickel, Raney nickel and platinum-Raney nickel; cobalt catalysts such as Raney cobalt; ruthenium catalysts such as ruthenium oxide and ruthenium/active carbon; rhodium catalysts such as rhodium/active carbon, rhodium/alumina and rhodium-platinum oxide; iridium catalysts such as iridium black; and palladium catalysts such as palladium/active carbon, palladium hydroxide, palladium black, palladium/barium sulfate, palladium/strontium carbonate, palladium/calcium carbonate, palladium/calcium carbonate-lead diacetate, palladium/barium sulfate-quinoline, palladium/alumina, palladium sponge, palladium chloride, palladium acetate, palladium acetylacetonate, bis(dibenzylideneacetone)palladium, tetrakis(triphenylphosphine)palladium, dichloro[bis(triphenylphosphine)]palladium, dichloro[bis(diphenylphosphino)methane]palladium, dichloro[bis(diphenylphosphino)ethane]palladium, dichloro[1,3-bis(diphenylphosphino)propane]palladium, dichloro[1,4bis(diphenylphosphino)butane]palladium, dichloro(1,5-cyclooctadiene)palladium, dichloro[bis(benzonitrile)]palladium, dichloro[bis(acetonitrile)]palladium and [bis(triphenylphosphine)]palladium acetate. Among them, platinum catalysts, nickel catalysts, ruthenium catalysts, rhodium catalysts and palladium catalysts are preferred. More preferred are platinum/active carbon, Raney nickel, ruthenium/active carbon, rhodium/active carbon and palladium/active carbon. These transition metal catalysts can be used alone or in combination thereof. In the case of using a catalyst material in which the transition metal is supported on any catalyst support, the amount of the metal supported is generally 0.1 to 50 wt %, preferably 0.5 to 30 wt %, more preferably 1 to 20 wt %. In order to enhance handling safety and prevent metal surface oxidation, the catalyst may be stored in water or mineral oil before use.

There is no particular restriction on the amount of the transition metal catalyst of Group VIII used, and it suffices to use the transition metal catalyst in an effective amount, generally preferably in an amount of 0.00001 to 0.1 g, more preferably 0.00005 to 0.05 g, in terms of the metal, relative to 1 g of the optically active imine of the formula [9].

There is no particular restriction on the amount of hydrogen used, and it suffices to use hydrogen in an amount of 0.8 mol or greater, relative to 1 mol of the optically active imine of the formula [9], generally in an excessive amount so as to conduct the asymmetric hydrogenation reaction under hydrogen atmosphere.

The hydrogen pressure of the hydrogen atmosphere is generally 5 MPa or lower, preferably 0.01 to 3 MPa, more preferably 0.05 to 2 MPa.

As the reaction solvent, there can be used: aliphatic hydrocarbons such as n-pentane, n-hexane, cyclohexane and n-heptane; aromatic hydrocarbons such as benzene, toluene, ethylbenzene, xylene and mesitylene; ethers such as diethyl ether, tetrahydrofuran, tert-butyl methyl ether and 1,4-dioxane; esters such as ethyl acetate and n-butyl acetate; alcohols such as methanol, ethanol, n-propanol, i-propanol, n-butanol, n-entanol, n-hexanol, cyclohexanol, n-heptanol, and n-octanol; and water. Among them, toluene, tetrahydrofuran, ethyl acetate, methanol, ethanol, n-propanol, i-propanol, n-butanol, n-pentanol, n-hexanol, cyclohexanol, n-heptanol, n-octanol and water are preferred. More preferred are methanol, ethanol, n-propanol, i-propanol, n-butanol, n-pentanol, n-hexanol, cyclohexanol, n-heptanol, n-octanol and water. These reaction solvents can be used alone or in combination thereof.

There is no particular restriction on the amount of the reaction solvent used, and it suffices to use the reaction solvent in an amount of 0.01 L or greater, generally preferably 0.05 to 20 L, more preferably 0.1 to 10 L, relative to 1 mol of the optically active imine of the formula [9].

The temperature condition is generally −60 to +100° C., preferably −40 to +75° C., more preferably −20 to +50° C.

The reaction time is generally 0.1 to 120 hours, but it varies depending on the reaction substrate and conditions. It is thus preferable to trace the progress of the reaction by any analytical means such as gas chromatography, liquid chromatography or NMR, and then, determine as a reaction end point the time at which the raw substrate material has almost disappeared.

Although the post-treatment is not particularly limited, the diastereomeric mixture of the optically active imine of the formula [10] is obtained as a crude product by performing a normal post-treatment operation after the termination of the asymmetric hydrogenation reaction. Further, the diastereomeric mixture of the optically active imine of the formula [10] can be obtained at high purity by subjecting the crude product to any purification operation such as activated carbon treatment, distillation, recrystallization and/or column chromatography as needed.

The process of asymmetric reduction of the optically active imine by the use of the hydride reducing agent will be next explained in detail.

Specific examples of the hydride reducing agent include: aluminum hydrides such as $(i\text{-Bu})_2\text{AlH}$, $(i\text{-Bu})_3\text{Al}$, $[2,6\text{-(tert-Bu)}_2\text{-4-MePh}]\text{Al}(i\text{-Bu})_2$, $\text{LiAlH}_4$, $\text{LiAlH(OMe)}_3$, $\text{LiAlH(O-tert-Bu)}_3$ and $\text{NaAlH}_2(\text{OCH}_2\text{CH}_2\text{OCH}_3)_2$; boron hydrides such as diborane, $\text{BH}_3.\text{THF}$, $\text{BH}_3.\text{SMe}$, $\text{BH}_3.\text{NMe}$, 9-BBN, $\text{NaBH}_4$, $\text{NaBH}_4\text{-CeCl}_3$, $\text{LiBH}_4$, $\text{Zn(BH}_4)_2$, $\text{Ca(BH}_4)_2$, $\text{LinBuBH}_3$, $\text{NaBH(OMe)}_3$, $\text{NaBH(OAc)}_3$, $\text{NaBH}_3\text{CN}$, $\text{Et}_4\text{NBH}_4$, $\text{Me}_4\text{NBH(OAc)}_3$, $(n\text{-Bu})_4\text{NBH}_3\text{CN}$, $(n\text{-Bu})_4\text{NBH(OAc)}_3$, $\text{Li(sec-Bu)}_3\text{BH}$, $\text{K(sec-Bu)}_3\text{BH}$, $\text{LiSia}_3\text{BH}$, $\text{KSia}_3\text{BH}$, $\text{LiEt}_3\text{BH}$, $\text{KPh}_3\text{BH}$, $(\text{Ph}_3\text{P})_2\text{CuBH}_4$, $\text{ThxBH}_2$, $\text{Sia}_2\text{BH}$, catecholborane, $\text{IpcBH}_2$ and $\text{Ipc}_2\text{BH}$; and silicon hydrides such as $\text{Et}_3\text{SiH}$, $\text{PhMe}_2\text{SiH}$, $\text{Ph}_2\text{SiH}_2$ and $\text{PhSiH}_3\text{-Mo(CO)}_6$, where Bu represents butyl; Ph represents phenyl; Me represents methyl; THF represents tetrahydrofuran; 9-BBN represents 9-borabicyclo[3,3,1]nonane; Ac represents acetyl; Sia represents siamyl; Et represents ethyl; Thx represents thexyl; and Ipc represents isopinocamphenyl. Among them, $\text{LiAlH}_4$, $\text{LiAlH(O-tert-Bu)}_3$, $\text{NaAlH}_2(\text{OCH}_2\text{CH}_2\text{OCH}_3)_2$, diborane, 9-BBN, $\text{NaBH}_4$, $\text{LiBH}_4$ and $\text{NaBH}_3\text{CN}$ are preferred. More preferred are $\text{LiAlH}_4$, $\text{NaAlH}_2(\text{OCH}_2\text{CH}_2\text{OCH}_3)_2$, diborane, $\text{NaBH}_4$, $\text{LiBH}_4$ and $\text{NaBH}_3\text{CN}$. These hydride reducing agents can be used in the presence of inorganic salts.

There is no particular restriction on the amount of the hydride reducing agent used, and it suffices to use the hydride reducing agent in an amount of 0.25 mol or greater, preferably 0.3 to 10 mols, more preferably 0.4 to 7 mols, relative to the optically active imine of the formula [9].

As the reaction solvent, there can be used: aliphatic hydrocarbons such as n-pentane, n-hexane, cyclohexane and n-heptane; aromatic hydrocarbons such as benzene, toluene, ethylbenzene, xylene and mesitylene; halogenated hydrocarbons such as methylene chloride, chloroform and 1,2-dichloroethane; ethers such as diethyl ether, tetrahydrofuran, tert-butyl methyl ether and 1,4-dioxane; and alcohols such as methanol, ethanol, n-propanol, i-propanol, n-butanol, n-pentanol, n-hexanol, cyclohexanol, n-heptanol, and n-octanol. Among them, n-heptane, toluene, methylene chloride, diethyl ether, tetrahydrofuran, tertbutyl methyl ether, methanol, ethanol, n-propanol and i-propanol are preferred. More preferred are toluene, tetrahydrofuran, tert-butyl methyl ether, methanol, ethanol and i-propanol. These reaction solvents can be used alone or in combination thereof.

There is no particular restriction on the amount of the reaction solvent used, and it suffices to use the reaction in an amount of 0.01 L or greater, generally preferably 0.05 to 20 L, more preferably 0.1 to 10 L, relative to 1 mol of the optically active imine of the formula [9].

The temperature condition is generally −100 to +100° C., preferably −80 to +85° C., more preferably −60 to +60° C.

The reaction time is generally 0.1 to 120 hours, but it varies depending on the reaction substrate and conditions. It is thus preferable to trace the progress of the reaction by any analytical means such as gas chromatography, liquid chromatography or NMR, and then, determine as a reaction end point the time at which the raw substrate material has almost disappeared. The post-treatment is not particularly limited. The diastereomeric mixture of the optically active imine of the formula [10] is obtained as a crude product by conducting a normal post-treatment operation after the termination of the asymmetric hydrogenation reaction. Further, the diastereomeric mixture of the optically active imine of the formula [10] can be obtained at high purity by subjecting the crude product to any purification operation such as activated carbon treatment, distillation, recrystallization and/or column chromatography as needed.

The third step: "salt purification" will be described below in detail. The salt purification of the third step is conducted by deriving a salt from the diastereomeric mixture of the optically active secondary amine of the formula [10] and purifying the salt by recrystallization.

As the acid of the salt, there can be used inorganic acids and organic acids.

Specific examples of the inorganic acids include: carbonic acid, hydrochloric acid, sulfuric acid, nitric acid, hydrobromic acid, hydroiodic acid, phosphoric acid, boric acid and perchloric acid. Among them, hydrochloric acid, sulfuric acid, nitric acid and hydrobromic acid are preferred. More preferred are hydrochloric acid and hydrobromic acid.

Specific examples of the organic acids include: aliphatic carboxylic acids such as acetic acid, propionic acid, butyric acid, isobutyric acid, valeric acid, isovaleric acid, hexanoic acid, heptanoic acid, cyclohexanecarboxylic acid, octanoic acid, phenylacetic acid and 3-phenylpropionic acid; haloalkylcarboxylic acids such as chloroacetic acid, dichloroacetic acid, trichloroacetic acid, fluoroacetic acid, difluoroacetic acid, trifluoroacetic acid, bromoacetic acid, iodoacetic acid, 2-chloropropionic acid and 3-chloropropionic acid; unsaturated carboxylic acids such as acrylic acid, crotonic acid, citraconic acid, maleic acid, fumaric acid and cis- or trans-cinnamic acid; aromatic carboxylic acids such as benzoic acid, o-, m- or p-toluic acid, o-, m- or p-fluorobenzoic acid, o-, m- or p-chlorobenzoic acid, o-, m- or p-bromobenzoic acid, o-, m- or p-iodobenzoic acid, o, m- or p-hydroxybenzoic acid, o-, m- or p-anisic acid, o-, m- or peminobenzoic acid, o-, m- or p-nitrobenzoic acid, o-, m- or p-cyanobenzoic acid, o-, m- or p-benzenedicarboxylic acid (phthalic acid, isophthalic acid or terephthalic acid), α-, β- or γ-picolinic acid, 2,6-pyridinedicarboxylic acid and 1- or 2-naphthoic acid; sulfonic acids such as methanesulfonic acid, chloromethanesulfonic acid, trifluoromethanesulfonic acid, benzenesulfonic acid, p-toluenesulfonic acid and p-phenolsulfonic acid; and other organic acid compounds such as formic acid, oxalic acid, malonic acid, succinic acid, adipic acid, pimelic acid, cyanoacetic acid, citric acid, glycolic acid, glyoxalic acid, pyruvic acid, levulinic acid, oxaloacetic acid, mercaptoacetic acid, phenoxyacetic acid and picric acid. Among them, cyclohexanecarboxylic acid, maleic acid, fumaric acid, o-, m- or p-bromobenzoic acid, o-, m- or p-ntrobenzoic acid, o-, m- or p-benzenedicarboxylic acid (phthalic acid, isophthalic acid or terephthalic acid), 1- or 2-naphthoic acid, benzenesulfonic acid, p-toluenesulfonic acid, oxalic acid, succinic acid and citric acid are preferred. More preferred are o-, m- or p-benzenedicarboxylic acid (phthalic acid, isophthalic acid or terephthalic acid), benzenesulfonic acid, p-toluenesulfonic acid and oxalic acid.

There is no particular restriction on the amount of the acid used, and it suffices to use the acid in an amount of 0.3 mol or greater, generally preferably 0.4 to 10 mols, more preferably 0.5 to 5 mols, relative to 1 mol of the diastereomeric mixture of the optically active secondary amine of the formula [10].

The preparation process of the salt can be suitably selected depending on the combination of the diastereomeric mixture of the optically active secondary amine of the formula [10] and the acid. In general, the salt can be prepared by directly adding the diastereomeric mixture of the optically active secondary amine of the formula [10] and the acid to a recrystallization solvent and mixing the solution, or by previously preparing the respective solutions and mixing the solutions into one. The precipitation of the salt crystals can be conducted directly from the prepared salt solution or by once concentrating the prepared salt solution, followed by dissolution again in the recrystallization solvent.

There is no particular restriction on the recrystallization solvent as long as it does not react with the diasteremeric mixture of the optically active secondary amine of the formula [10], the acid and the salt prepared therefrom. The recrystallization solvent can be suitably selected depending on the diastereomer excess of the unpurified salt, the target diastereomer excess of the purified salt, the recovery rate and the like.

As the recrystallization solvent, there can be used: aliphatic hydrocarbons such as n-pentane, n-exane, cyclohexane and n-heptane; aromatic hydrocarbons such as benzene, toluene, ethylbenzene, xylene and mesitylene; halogenated hydrocarbons such as methylene chloride, chloroform and 1,2-dichloroethane; ethers such as diethyl ether, tetrahydrofuran, tert-butyl methyl ether and 1,4-dioxane; ketones such as acetone, methyl ethyl ketone and methyl isobutyl ketone; esters such as ethyl acetate and n-butyl acetate; nitriles such as acetonitrile and propionitrile; alcohols such as methanol, ethanol, n-propanol, i-propanol and n-butanol; and water. Among them, n-hexane, n-heptane, toluene, methylene chloride, tetrahydrofuran, tertbutyl methyl ether, acetone, methyl ethyl ketone, ethyl acetate, acetonitrile, methanol, ethanol, n-propanol and i-propanol are preferred. More preferred are n-hexane, n-heptane, toluene, tetrahydrofuran, acetone, methanol, ethanol, n-propanol and i-propanol. These recrystallization solvents can be used alone or in combination thereof.

There is no particular restriction on the amount of the recrystallization solvent used as long as the unpurified salt is completely or partially dissolved in the recrystallization solvent upon heating. The recrystallization solvent amount can be suitably selected depending on the diastereomer excess of the unpurified salt, the target diastereomer excess of the purified salt, the recovery rate and the like. It suffices to use the recrystallization solvent in an amount of 0.01 L or greater, generally preferably 0.05 to 50 L, more preferably 0.1 to 25 L, relative to 1 mol of the unpurified salt derived from the diastereomeric mixture of the optically active secondary amine of the formula [10].

There is no particular restriction on the combination of the absolute configurations at two asymmetric carbons of the diastereomeric mixture of the optically active secondary amine of the formula [10]. There exist any of R—R configuration, S—R configuration, R—S configuration and S—S configuration isomers. Among them, R—R configuration and S—S configuration isomers can be purified efficiently by salt purification so that it is advantageous to use the diastereomeric mixture containing these configuration isomers in greater amounts for the salt purification.

There is no particular restriction on the diastereomer excess of the diastereomeric mixture of the optically active secondary amine of the formula [10] to be subjected to the salt purification, and it suffices that the diastereomeric mixture of the optically active secondary amine of the formula [10] has a diastereomer excess (d.e.) of 5% d.e. or greater, generally preferably 10% d.e. or greater, more preferably 15% d.e. or greater.

The salt can be crystallized out by adding a seed crystal in this purification step. There is no particular restriction on the diastereomer excess of the seed crystal, and it suffices that the seed crystal has a diastereomer excess of 95% d.e. or greater, generally preferably 97% d.e. or greater, more preferably 99% d.e. or greater.

Further, it suffices to use the seed crystal in an amount of 0.00005 mol or greater, generally preferably 0.0001 to 0.1 mol, more preferably 0.0005 to 0.05 mol, relative to 1 mol of the unpurified salt derived from the diastereomeric mixture of the optically active secondary amine of the formula [10].

The temperature condition is suitably selected depending on the boiling and freezing points of the recrystallization solvent used. It is preferable to dissolve the unpurified salt at around a temperature between room temperature (25° C.) and the boiling point of the recrystallization solvent, gradually decrease the temperature of the solution and then crystallize out the salt at −20 to +20° C. sufficiently. It is further preferable to add the seed crystal during the temperature decrease.

In general, the diastereomer excess of the crystallized salt is increased through the purification step. The salt can be thus obtained at a high diastereomer excess by recovering the precipitated crystals by filtration etc. Depending on the depending on the combination of the diastereomeric mixture of the optically active secondary amine of the formula [10] and the acid, the diastereomer excess of the mother liquor may be increased. In such a case, the solution containing the salt at a high diastereomer excess can be obtained by removing the precipitated crystals by filtration etc. Further, the salt can be purified to a higher diastereomer excess by repeating the above purification operations.

The salt purified by recrystallization may be used directly, or used after neutralized to a free base, in the subsequent hydrogenolysis step. In the neutralization process, the free base can be recovered efficiently by neutralizing the salt with an aqueous solution of inorganic base such as sodium hydroxide or potassium hydroxide, followed by extraction with an organic solvent.

Finally, the fourth step: "hydrogenolysis" will be described below in detail. The hydrogenolysis of the fourth step is conducted by subjecting the optically active secondary amine of the formula [1] or its salt to hydrogenolysis in the presence of the transition metal catalyst of Group VIII.

In the hydrogenolysis step, it is possible to produce the optically active 1-aryl-2-fluoro-substituted ethyl amine compound of the formula [2] or its salt in R configuration, with no loss of optical purity, from the R—R configuration and R—S configuration isomers of the optically active secondary amine compound of the formula [1] or its salt. It is also possible to produce the optically active 1-aryl-2-fluoro-substituted ethyl amine compound of the formula [2] or its salt in S configuration, with no loss of optical purity, from the S—R configuration and S—S configuration isomers of the optically active secondary amine compound of the formula [1] or its salt.

For the hydrogenolysis of the fourth step, there may be used the same reaction conditions as those for the asymmetric hydrogenation of the optically active imine in the presence of the transition metal catalyst of Group VIII during the asymmetric reduction of the second step. In this case, the reaction conditions are determined by replacing the optically active imine of the formula [9] with the optically active secondary amine compound of the formula [1] or its salt and replacing the diastereomeric mixture of the optically active secondary amine of the formula [10] with the optically active 1-aryl-2-fluro-substituted ethyl amine compound of the formula [2] or its salt. A similar explanation of the hydrogenolysis reaction conditions (e.g. the kind of the transition metal catalyst of Group VIII, the amount of the transmission metal catalyst of Group VIII used, the amount of hydrogen used, the hydrogen pressure of hydrogen atmosphere, the kind of the reaction solvent, the amount of the reaction solvent used and the reaction time) will be thus omitted. Herein, the reaction conditions for the hydrogenolysis of the fourth step significantly differ from those for the asymmetric hydrogenation of the asymmetric reduction of the second step in some items such as the temperature condition, acid addition and post-treatment. A detail explanation of these items will be given below.

It is efficient and effective to set the temperature condition of the hydrogenolysis step at a temperature higher than the temperature condition of the asymmetric hydrogenation of the optically active imine in the presence of the transition metal catalyst of Group VIII. The hydrogenolysis temperature condition is generally 10 to 200° C., preferably 20 to 150° C., more preferably 30 to 100° C.

Upon addition of an acid catalyst, the hydrogenolysis reaction proceeds at high selectivity with almost no side reaction.

As the acid catalyst, there can be used the same inorganic and organic acids as mentioned in the explanation of the salt purification of the third step.

There is no particular restriction on the amount of the acid catalyst used, and it suffices to use the acid catalyst in an amount of 0.8 mol or greater, generally preferably 0.9 to 20 mols, more preferably 1.0 to 15 mols, relative to 1 mol of the optically active secondary amine compound of the formula [1] or its salt.

Although the post-treatment is not particularly limited, the optically active 1-aryl-2-fluoro-substituted ethylamine of the formula [2] or its salt is obtained as a crude product by conducting a normal post-treatment operation after the termination of the hydrogenolysis reaction. In particular, the optically active 1-aryl-2-fluoro-substituted ethylamine is obtained in salt form in the case of using as a raw hydrogenolysis reaction substrate the amine salt purified by recrystallization in the third step or in the case of carrying out the hydrogenolysis reaction upon addition of the acid to the free base. The unreacted optically active 1-phenylethylamine can be selectively removed by washing the reaction-terminated liquid or organic phase containing the target optically active imine of the formula [9] with an ammonium chloride aqueous solution. The thus-obtained salt may be purified by recrystallization. The free base of the optically active 1-aryl-2-fluoro-substituted amine can be recovered efficiently by neutralizing the salt with an aqueous solution of inorganic base such as sodium hydroxide or potassium hydroxide, followed by extraction with an organic solvent. Further, the optically active 1-aryl-2-fluoro-substituted ethylamine of the formula [2] or its salt can be obtained at high purity by subjecting the crude product to any purification operation such as activated carbon treatment, distillation, recrystallization and/or column chromatography as needed.

Specific examples of the optically active 1-aryl-2-fluoro-substituted ethylamine represented by the formula [2] according to the present invention include (R or S)-1-phenyl-2-monofluoroethylamine, (R or S)-1-[1'-(2'-, 3'- or 4'-methyl)phenyl]-2-monofluoroethylamine, (R or S)-1-[1'-(2'-, 3'- or 4'-ethyl)phenyl]-2-monofluoroethylamine, (R or S)-1-[1'-(2'-, 3'- or 4'-fluoro)phenyl]-2-monofluoroethylamine, (R or S)-1-[1'-(2'-, 3'- or 4'-chloro)phenyl]-2-monofluoroethylamine, (R or S)-1-[1'-(2'-, 3'- or 4'-trifluoromethyl)phenyl]-2-monofluoroethylamine, (R or S)-1-[1'-(2'-, 3'- or 4'-pentafluoroethyl)phenyl]-2-monofluoroethylamine, (R or S)-1-[1'-(2'-, 3'- or 4'-methoxy)phenyl]-2-monofluoroethylamine, (R or S)-1-[1'-(2'-, 3'- or 4'-ethoxy)phenyl]-2-monofluoroethylamine, (R or S)-1-[1'-(2'-, 3'- or 4'-trifluoromethoxy)phenyl]-2-monofluoroethylamine, (R or S)-1-[1'-(2'-, 3'- or 4'-pentafluoroethoxy)phenyl]-2-monofluoroethylamine, (R or S)-1-[1'-(2'-, 3'- or 4'-methylamino)phenyl]-2-monofluoroethylamine, (R or S)-1-[1'-(2'-, 3'- or 4'-dimethylamino)phenyl]-2-monofluoroethylamine, (R or S)-1-[1'-(2'-, 3'- or 4'-methylthio)phenyl]-2-monofluoroethylamine, (R or S)-1-[1'-(2'-, 3'- or 4'-ethylthio)phenyl]-2-monofluoroethylamine, (R or S)-1-phenyl-2-difluoroethylamine, (R or S)-1-[1'-(2'-, 3'- or 4'-methyl)phenyl]-2-difluoroethylamine, (R or S)-1-[1'-(2'-, 3'- or 4'-ethyl)phenyl]-2-difluoroethylamine, (R or S)-1-[1'-(2'-, 3'- or 4'-fluoro)phenyl]-2-difluoroethylamine, (R or S)-1-[1'-(2'-, 3'- or 4'-chloro)phenyl]-2-difluoroethylamine, (R or S)-1-[1'-(2'-, 3'- or 4'-trifluoromethyl)phenyl]-2-difluoroethylamine, (R or S)-1-[1'-(2'-, 3'- or 4'-pentafluoroethyl)phenyl]-2-difluoroethylamine, (R or S)-1-[1'-(2'-, 3'- or 4'-methoxy)phenyl]-2-difluoroethylamine, (R or S)-1-[1'-(2'-, 3'- or 4'-ethoxy)phenyl]-2-difluoroethylamine, (R or S)-1-[1'-(2'-, 3'- or 4'-trifluoromethoxy)phenyl]-2-difluoroethylamine, (R or S)-1-[1'-(2'-, 3'- or 4'-pentafluoroethoxy)phenyl]-2-difluoroethylamine, (R or S)-1-[1'-(2'-, 3'- or 4'-methylamino)phenyl]-2-difluoroethylamine, (R or S)-1-[1'-(2'-, 3'- or 4'-dimethylamino)phenyl]-2-difluoroethylamine, (R or S)-1-[1'-(2'-, 3'- or 4'-methylthio)phenyl]-2-difluoroethylamine, (R or S)-1-[1'-(2'-, 3'- or 4'-ethylthio)phenyl]-2-difluoroethylamine, (R or S)-1-(1'-naphthyl)-2-monofluoroethylamine, (R or S)-1-(2'-naphthyl)-2-monofluoroethylamine, (R or S)-1-[1'-(2'-, 3'-, 4'-, 5'-, 6'-, 7'- or 8'-methyl)naphthyl]-2-monofluoroethylamine, (R or S)-1-[2'-(1'-, 3'-, 4'-, 5'-, 6'-, 7'- or 8'-methyl)naphthyl]-2-monofluoroethylamine, (R or S)-1-[1'-(2'-, 3'-, 4'-, 5'-, 6'-, 7'- or 8'-ethyl)naphthyl]-2-monofluoroethylamine, (R or S)-1-[2'-(1'-, 3'-, 4'-, 5'-, 6'-, 7'- or 8'-ethyl)naphthyl]-2-monofluoroethylamine, (R or S)-1-[1'-( 2'-, 3'-, 4'-, 5'-, 6'-, 7'- or 8'-fluoro)naphthyl]-2-monofluoroethylamine, (R or S)-1-[2'-(1'-, 3'-, 4'-, 5'-, 6'-, 7'- or 8'-fluoro)naphthyl]-2-monofluoroethylamine, (R or S)-1-[1'-(2'-, 3'-, 4'-, 5'-, 6'-, 7'- or 8'-chloro)naphthyl]-2-monofluoroethylamine, (R or S)-1-[2'-(1'-, 3'-, 4'-, 5'-, 6'-, 7'- or 8'-chloro)naphthyl]-2-monofluoroethylamine, (R or S)-1-[1'-(2'-, 3'-, 4'-, 5'-, 6'-, 7'- or 8'-trifluoromethyl)naphthyl]-2-monofluoroethylamine, (R or S)-1-[2'-(1'-, 3'-, 4'-, 5'-, 6'-, 7'- or 8'-fluoromethyl)naphthyl]-2-monofluoroethylamine, (R or S)-1-[1'-(2'-, 3'-, 4'-, 5'-, 6'-, 7'- or 8'-pentafluoroethyl)naphthyl]-2-monofluoroethylamine, (R or S)-1-[2'-(1'-, 3'-, 4'-, 5'-, 6'-, 7'- or 8'-pentafluoroethyl)naphthyl]-2-monofluoroethylamine, (R or S)-1-[1'-(2'-, 3'-, 4'-, 5'-, 6'-, 7'- or 8'-methoxy)naphthyl]-2-monofluoroethylamine, (R or S)-1-[2'-(1'-, 3'-, 4'-, 5'-, 6'-, 7'- or 8'-methoxy)naphthyl]-2-monofluoroethylamine, (R or S)-1-[1'-(2'-, 3'-, 4'-, 5'-, 6'-, 7'- or 8'-ethoxy)naphthyl]-2-monofluoroethylamine, (R or S)-1-[2'-(1'-, 3'-, 4'-, 5'-, 6'-, 7'- or 8'-ethoxy)naphthyl]-2-monofluoroethylamine, (R or S)-1-[1'-(2'-, 3'-, 4'-, 5'-, 6'-, 7'- or 8'-trifluoromethoxy)naphthyl]-2-monofluoroethylamine, (R or S)-1-[2'-(1'-, 3'-, 4'-, 5'-, 6'-, 7'- or 8'-trifluoromethoxy)naphthyl]-2-monofluoroethylamine, (R or S)-1-[1'-(2'-, 3'-, 4'-, 5'-, 6'-, 7'- or 8'-pentafluoroethoxy)naphthyl]-2-monofluoroethylamine, (R or S)-1-[2'-, (1'-, 3'-, 4'-, 5'-, 6'-, 7'- or 8'-pentafluoroethoxy)naphthyl]-2-monofluoroethylamine,
(R or S)-1-[1'-(2'-, 3'-, 4'-, 5'-, 6'-, 7'- or 8'-methylamino)naphthyl]-2-monofluoroethylamine, (R or S)-1-[2'-(1'-, 3'-, 4'-, 5'-, 6'-, 7'- or 8'-methylamino)naphthyl]-2-monofluoroethylamine, (R or S)-1-[1'-(2'-, 3'-, 4'-, 5'-, 6'-, 7'- or 8'-dimethylamino)naphthyl]-2-monofluoroethylamine, (R or S)-1-[2'-(1'-, 3'-, 4'-, 5'-, 6'-, 7'- or 8'-dimethylamino)naphthyl]-2-monofluoroethylamine, (R or S)-1-[1'-(2'-, 3'-, 4'-, 5'-, 6'-, 7'- or 8'-methylthio)naphthyl]-2-monofluoroethylamine, (R or S)-1-[2'-(1'-, 3'-, 4'-, 5'-, 6'-, 7'- or 8'-methylthio)naphthyl]-2-monofluoroethylamine, (R or S)-1-[1'-(2'-, 3'-, 4'-, 5'-, 6'-, 7'- or 8'-ethylthio)naphthyl]-2-monofluoroethylamine, (R or S)-1-[2'-(1'-, 3'-, 4'-, 5'-, 6'-, 7'- or 8'-ethylthio)naphthyl]-2-monofluoroethylamine, (R or S)-1-(1'-naphthyl)-2-difluoroethylamine, (R or S)-1-(2'-naphthyl)-2-difluoroethylamine, (R or S)-1-[1'-(2'-, 3'-, 4'-, 5'-, 6'-, 7'- or 8'-methyl)naphthyl]-2-difluoroethylamine, (R or S)-1-[2'-(1'-, 3'-, 4'-, 5'-, 6'-, 7'- or 8'-methyl)naphthyl]-2-difluoroethylamine, (R or S)-1-[1'-(2'-, 3'-, 4'-, 5'-, 6'-, 7'- or 8'-ethyl)naphthyl]-2-difluoroethylamine, (R or S)-1-[2'-(1'-, 3'-, 4'-, 5'-, 6'-, 7'- or 8'-ethyl)naphthyl]-2-difluoroethylamine, (R or S)-1-[1'-(2'-, 3'-, 4'-, 5'-, 6'-, 7'- or 8'-fluoro)naphthyl]-2-difluoroethylamine, (R or S)-1-[2'-(1'-, 3'-, 4'-, 5'-, 6'-, 7'- or 8'-fluoro)naphthyl]-2-difluoroethylamine, (R or S)-1-[1'-(2'-, 3'-, 4'-, 5'-, 6'-, 7'- or 8'-chloro)naphthyl]-2-difluoroethylamine, (R or S)-1-[2'-(1'-, 3'-, 4'-, 5'-, 6'-, 7'- or 8'-chloro)naphthyl]-2-difluoroethylamine, (R or S)-1-[1'-(2'-, 3'-, 4'-, 5'-, 6'-, 7'- or 8'-trifluoromethyl)naphthyl]-2-difluoroethylamine, (R or S)-1-[2'-(1'-, 3'-, 4'-, 5'-, 6'-, 7'- or 8'-trifluoromethyl)naphthyl] -2-difluoroethylamine, (R or S)-1-[1'-(2'-, 3'-, 4'-, 5'-, 6'-, 7'- or 8'-pentafluoroethyl)naphthyl]-2-difluoroethylamine, (R or S)-1-[2'-(1'-, 3'-, 4'-, 5'-, 6'-, 7'- or 8'-pentafluoroethyl)naphthyl]-2-difluoroethylamine, (R or S)-1-[1'-(2'-, 3'-, 4'-, 5'-, 6'-, 7'- or 8'-methoxy)naphthyl]-2-difluoroethylamine, (R or S)-1-[2'-(1'-, 3'-, 4'-, 5'-, 6'-, 7'- or 8'-methoxy)naphthyl]-2-difluoroethylamine, (R or S)-1-[1'-(2'-, 3'-, 4'-, 5'-, 6'-, 7'- or 8'-ethoxy)naphthyl]-2-difluoroethylamine, (R or S)-1-[2'-(1'-, 3'-, 4'-, 5'-, 6'-, 7'- or 8'-ethoxy)naphthyl]-2-difluoroethylamine, (R or S)-1-[1'-(2'-, 3'-, 4'-, 5'-, 6'-, 7'- or 8'-trifluoromethoxy)naphthyl]-2-difluoroethylamine, (R or S)-1-[2'-(1'-, 3'-, 4'-, 5'-, 6'-, 7'- or 8'-fluoromethoxy)naphthyl]-2-difluoroethylamine, (R or S)-1-[1'-(2'-, 3'-, 4'-, 5'-, 6'-, 7'- or 8'-pentafluoroethoxy)naphthyl]-2-difluoroethylamine, (R or S)-1-[2'-(1'-, 3'-, 4'-, 5'-, 6'-, 7'- or 8'-pentafluoroethoxy)naphthyl]-2-difluoroethylamine, (R or S)-1-[1'-(2'-, 3'-, 4'-, 5'-, 6'-, 7'- or 8'-methylamino)naphthyl]-2-difluoroethylamine, (R or S)-1-[2'-(1'-, 3'-, 4'-, 5'-, 6'-, 7'- or 8'-methylamino)naphthyl]-2-difluoroethylamine, (R or S)-1-[1'-(2'-, 3'-, 4'-, 5'-, 6'-, 7'- or 8'-dimethylamino)naphthyl]-2-difluoroethylamine, (R or S)-1-[2'-(1'-, 3'-, 4'-, 5'-, 6'-, 7'- or 8'-dimethylamino)naphthyl] -2-difluoroethylamine, (R or S)-1-[1'-(2'-, 3'-, 4'-, 5'-, 6'-, 7'- or 8'-methylthio)naphthyl]-2-difluoroethylamine, (R or S)-1-[2'-(1'-, 3'-, 4'-, 5'-, 6'-, 7'- or 8'-methylthio)naphthyl]-2-difluoroethylamine, (R or S)-1-[1'-(2'-, 3'-, 4'-, 5'-, 6'-, 7'- or 8'-ethylthio)naphthyl]-2-difluoroethylamine, (R or S)-1-[2'-(1'-, 3'-, 4'-, 5'-, 6'-, 7'- or 8'-ethylthio)naphthyl]-2-difluoroethylamine, (R or S)-1-(2'-furyl)-2-monofluoroethylamine, (R or S)-1-(3'-furyl)-2-monofluoroethylamine, (R or S)-1-[2'-(3'-, 4'- or 5'-methyl)furyl]-2-monofluoroethylamine, (R or S)-1-[3'-(2'-, 4'- or 5'-methyl)furyl]-2-monofluoroethylamine, (R or S)-1-[2'-(3'-, 4'- or 5'-ethyl)furyl]-2-monofluoroethylamine, (R or S)-1-[3'-(2'-, 4'- or 5'-ethyl)furyl]-2-monofluoroethylamine, (R or S)-1[-2'-(3'-, 4'- or 5'-fluoro)furyl]-2-monofluoroethylamine, (R or S)-1-[3'-(2'-, 4'- or 5'-fluoro)furyl]-2-monofluoroethylamine, (R or S)-1-[2'-(3'-, 4'- or 5'-chloro)furyl]-2-monofluoroethylamine, (R or S)-1-[3'-(2'-, 4'- or 5'-chloro)furyl]-2-monofluoroethylamine, (R or S)-1-[2'-(3'-, 4'- or 5'-trifluoromethyl)furyl]-2-monofluoroethylamine, (R or S)-1-[3'-(2'-, 4'- or 5'-trifluoromethyl)furyl]-2-monofluoroethylamine, (R or S)-1-[2'-(3'-, 4'- or 5'-pentafluoroethyl)furyl]-2-monofluoroethylamine, (R or S)-1-[3'-(2'-, 4'- or 5'-pentafluoroethyl)furyl]-2-monofluoroethylamine, (R or S)-1-[2'-(3'-, 4'- or 5'-methoxy)furyl]-2-monofluoroethylamine, (R or S)-1-[3'-(2'-, 4'- or 5'-methoxy)furyl]-2-monofluoroethylamine, (R or S)-1-[2'-(3'-, 4'- or 5'-ethoxy)furyl]-2-monofluoroethylamine, (R or S)-1-[3'-(2'-, 4'- or 5'-ethoxy)furyl]-2-monofluoroethylamine, (R or S)-1-[2'-(3'-, 4'- or 5'-trifluoromethoxy)furyl]-2-monofluoroethylamine, (R or S)-1-[3'-(2'-, 4'- or 5'-trifluoromethoxy)furyl]-2-monofluoroethylamine, (R or S)-1-[2'-(3'-, 4'- or 5'-pentafluoroethoxy)furyl]-2-monofluoroethylamine, (R or S)-1-[3'-(2'-, 4'- or 5'-pentafluoroethoxy)furyl]-2-monofluoroethylamine, (R or S)-1-[2'-(3'-, 4'- or 5'-methylamino)furyl]-2-monofluoroethylamine, (R or S)-1-[3'-(2'-, 4'- or 5'-methylamino)furyl]-2-monofluoroethylamine, (R or S)-1-[2'-(3'-, 4'- or 5'-dimethylamino)furyl]-2-monofluoroethylamine, (R or S)-1-[3'-(2'-, 4'- or 5'-dimethylamino)furyl]-2-monofluoroethylamine, (R or S)-1-[2'-(3'-, 4'- or 5'-methylthio)furyl]-2-monofluoroethylamine, (R or S)-1-[3'-(2'-, 4'- or 5'-methylthio)furyl]-2-monofluoroethylamine, (R or S)-1-[2'-(3'-, 4'- or 5'-ethylthio)furyl]-2-monofluoroethylamine, (R or S)-1-[3'-(2'-, 4'- or 5'-ethylthio)furyl]-2-monofluoroethylamine, (R or S)-1-(2'-furyl)-2-difluoroethylamine, (R or S)-1-(3'-furyl)-2-difluoroethylamine, (R or S)-1-[2'-(3'-, 4'-, or 5'-methyl)furyl]-2-difluoroethylamine, (R or S)-1-[3'-(2'-, 4'- or 5'-methyl)furyl]-2-difluoroethylamine, (R or S)-1-[2'-(3'-, 4'- or 5'-ethyl)furyl]-2-difluoroethylamine, (R or S)-1-[3'-(2'-, 4'- or 5'-ethyl)furyl]-2-difluoroethylamine, (R or S)-1-[2'-(3'-, 4'- or 5'-fluoro)furyl]-2-difluoroethylamine, (R or S)-1-[3'-(2'-, 4'- or 5'-fluoro)furyl]-2-difluoroethylamine, (R or S)-1-[2'-(3'-, 4'- or 5'-chloro)furyl]-2-difluoroethylamine, (R or S)-1-[3'-(2'-, 4'- or 5'-chloro)furyl]-2-difluoroethylamine, (R or S)-1-[2'-(3'-, 4'- or 5'-trifluoromethyl)furyl]-2-difluoroethylamine, (R or S)-1-[3'-(2'-, 4'- or 5'-trifluoromethyl)furyl]-2-difluoroethylamine, (R or S)-1-[2'-(3'-, 4'- or 5'-pentafluoroethyl)furyl]-2-difluoroethylamine, (R or S)-1-[3'-(2'-, 4'- or 5'-pentafluoroethyl)furyl]-2-difluoroethylamine, (R or S)-1-[2'-(3'-, 4'- or 5'-methoxy)furyl]-2-difluoroethylamine, (R or S)-1-[3'-(2'-, 4'- or 5'-methoxy)furyl]-2-difluoroethylamine, (R or S)-1-[2'-(3'-, 4'- or 5'-ethoxy)furyl]-2-difluoroethylamine, (R or S)-1-[3'-(2'-, 4'- or 5'-ethoxy)furyl]-2-difluoroethylamine, (R or S)-1-[2'-(3'-, 4'- or 5'-trifluoromethoxy)furyl]-2-difluoroethylamine, (R or S)-1-[3'-(2'-, 4'- or 5'-trifluoromethoxy)furyl]-2-difluoroethylamine, (R or S)-1-[2'-(3'-, 4'- or 5'-pentafluoroethoxy)furyl]-2-difluoroethylamine, (R or S)-1-[3'-(2'-, 4'- or 5'-pentafluoroethoxy)furyl]-2-difluoroethylamine, (R or S)-1-[2'-(3'-, 4'- or 5'-methylamino)furyl]-2-difluoroethylamine, (R or S)-1-[3'-(2'-, 4'- or 5'-methylamino)furyl]-2-difluoroethylamine, (R or S)-1-[2'-(3'-, 4'- or 5'-dimethylamino)furyl]-2-difluoroethylamine, (R or S)-1-[3'-(2'-, 4'- or 5'-dimethylamino)furyl]-2-difluoroethylamine, (R or S)-1-[2'-(3'-, 4'- or 5'-methylthio)furyl]-2-difluoroethylamine, (R or S)-1-[3'-(2'-, 4'- or 5'-methylthio)furyl]-2-difluoroethylamine, (R or S)-1-[2'-(3'-, 4'- or 5'-ethylthio)furyl]-2-difluoroethylamine, (R or S)-1-[3'-(2'-, 4'- or 5'-ethylthio)furyl]-2-difluoroethylamine, (R or S)-1-(2'-pyridyl)-2-monofluoroethylamine, (R or S)-1-(3'-pyridyl)-2-monofluoroethylamine, (R or S)-1-(4'-pyridyl)-2-monofluoroethylamine, (R or S)-1-[2'-(3'-, 4'-, 5'- or 6'-methyl)pyridyl]-2-monofluoroethylamine, (R or S)-1-[3'-(2'-, 4'-, 5'- or 6'-methyl)pyridyl]-2-monofluoroethylamine, (R or S)-1-[4'-(2'- or 3'-methyl)pyridyl]-2-monofluoroethylamine, (R or S)-1-[2'-(3'-, 4'-, 5'- or 6'-ethyl)pyridyl]-2-monofluoroethylamine, (R or S)-1-[3'-(2'-, 4'-, 5'- or 6'-ethyl)pyridyl]-2-monofluoroethylamine, (R or S)-1-[4'-(2'- or 3'-ethyl)pyridyl]-2-monofluoroethylamine, (R or S)-1-[2'-(3'-, 4'-, 5'- or 6'-fluoro)pyridyl]-2-monofluoroethylamine, (R or S)-1-[3'-(2'-, 4'-, 5'- or 6'-fluoro)pyridyl]-2-monofluoroethylamine, (R or S)-1-[4'-(2'- or 3'-fluoro)pyridyl]-2-monofluoroethylamine, (R or S)-1-[2'-(3'-, 4'-, 5'- or 6'-chloro)pyridyl]-2-monofluoroethylamine, (R or S)-1-[3'-(2'-, 4'-, 5'- or 6'-chloro)pyridyl]-2-monofluoroethylamine, (R or S)-1-[4'-(2'- or 3'-chloro)pyridyl]-2-monofluoroethylamine, (R or S)-1-[2'-(3'-, 4'-, 5'- or 6'-trifluoromethyl)pyridyl]-2-monofluoroethylamine, (R or S)-1-[3'-(2'-, 4'-, 5'- or 6'-trifluoromethyl)pyridyl]-2-monofluoroethylamine, (R or S)-1-[4'-(2'- or 3'-trifluoromethyl)pyridyl]-2-monofluoroethylamine, (R or S)-1-[2'-(3'-, 4'-, 5'- or 6'-pentafluoroethyl)pyridyl]-2-monofluoroethylamine, (R or S)-1-[3'-(2'-, 4'-, 5'- or 6'-pentafluoroethyl)pyridyl]-2-monofluoroethylamine, (R or S)-1-[4'-(2'- or 3'-pentafluoroethyl)pyridyl]-2-monofluoroethylamine, (R or S)-1-[2'-(3'-, 4'-, 5'- or 6'-methoxy)pyridyl]-2-monofluoroethylamine, (R or S)-1-[3'-(2'-, 4'-, 5'- or 6'-methoxy)pyridyl]-2-monofluoroethylamine, (R or S)-1-[4'-(2'- or 3'-methoxy)pyridyl]-2-monofluoroethylamine, (R or S)-1-[2'-(3'-, 4'-, 5'- or 6'-ethoxy)pyridyl]-2-monofluoroethylamine, (R or S)-1-[3'-(2'-, 4'-, 5'- or 6'-ethoxy)pyridyl]-2-monofluoroethylamine, (R or S)-1-[4'-(2'- or 3'-ethoxy)pyridyl]-2-monofluoroethylamine, (R or S)-1-[2'-(3'-, 4'-, 5'- or 6'-trifluoromethoxy)pyridyl]-2-monofluoroethylamine, (R or S)-1-[3'-(2'-, 4'-, 5'- or 6'-trifluoromethoxy)pyridyl]-2-monofluoroethylamine, (R or S)-1-[4'-(2'- or 3'-trifluoromethoxy)pyridyl]-2-monofluoroethylamine, (R or S)-1-[2'-(3'-, 4'-, 5'- or 6'-pentafluoroethoxy)pyridyl]-2-monofluoroethylamine, (R or S)-1-[3'-(2'-, 4'-, 5'- or 6'-pentafluoroethoxy)pyridyl]-2-monofluoroethylamine, (R or S)-1-[4'-(2'- or 3'-pentafluoroethoxy)pyridyl]-2-monofluoroethylamine, (R or S)-1-[2'-(3'-, 4'-, 5'- or 6'-methylamino)pyridyl]-2-monofluoroethylamine, (R or S)-1-[3'-(2'-, 4'-, 5'- or 6'-methylamino)pyridyl]-2-monofluoroethylamine, (R or S)-1-[4'-(2'- or 3'-methylamino)pyridyl]-2-monofluoroethylamine, (R or S)-1-[2'-(3'-, 4'-, 5'- or 6'-dimethylamino)pyridyl]-2-monofluoroethylamine, (R or S)-1-[3'-(2'-, 4'-, 5'- or 6'-dimethylamino)pyridyl]-2-monofluoroethylamine, (R or S)-1-[4'-(2'- or 3'-dimethylamino)pyridyl]-2-monofluoroethylamine, (R or S)-1-[2'-(3'-, 4'-, 5'- or 6'-methylthio)pyridyl]-2-monofluoroethylamine, (R or S)-1-[3'-(2'-, 4'-, 5'-, or 6'-methylthio)pyridyl]-2-monofluoroethylamine, (R or S)-1-[4'-(2'- or 3'-methylthio)pyridyl]-2-monofluoroethylamine, (R or S)-1-[2'-(3'-, 4'-, 5'- or 6'-ethylthio)pyridyl]-2-monofluoroethylamine, (R or S)-1-[3'-(2'-, 4'-, 5'- or 6'-ethylthio)pyridyl]-2-monofluoroethylamine, (R or S)-1-[4'-(2'- or 3'-ethylthio)pyridyl]-2-monofluoroethylamine, (R or S)-1-(2'-pyridyl)-2-difluoroethylamine, (R or S)-1-(3'-pyridyl)-2-difluoroethylamine, (R or S)-1-(4'-pyridyl)-2-difluoroethylamine, (R or S)-1-[2'-(3'-, 4'-, 5'- or 6'-methyl)pyridyl]-2-difluoroethylamine, (R or S)-1-[2'-(3'-, 4'-, 5'- or 6'-methyl)pyridyl]-2-difluoroethylamine, (R or S)-1-[3'-(2'-, 4'-, 5'- or 6'-methyl)pyridyl]-2-difluoroethylamine, (R or S)-1-[4'-(2'- or 3'-methyl)pyridyl]-2-difluoroethylamine, (R or S)-1-[2'-(3'-, 4'-, 5'- or 6'-ethyl)pyridyl]-2-difluoroethylamine, (R or S)-1-[3'-(2'-, 4'-, 5'- or 6'-ethyl)pyridyl]-2-difluoroethylamine, (R or S)-1-[4'-(2'- or 3'-ethyl)pyridyl]-2-difluoroethylamine, (R or S)-1-[2'-(3'-, 4'-, 5'- or 6'-fluoro)pyridyl]-2-difluoroethylamine, (R or S)-1'-[3'-(2'-, 4'-, 5'- or 6'-fluoro)pyridyl]-2-difluoroethylamine, (R or S)-1-[4'-(2'- or 3'-fluoro)pyridyl]-2-difluoroethylamine, (R or S)-1-[2'-(3'-, 4'-, 5'- or 6'-chloro)pyridyl]-2-difluoroethylamine, (R or S)-1-[3'-(2'-, 4'-, 5'- or 6'-chloro)pyridyl]-2-difluoroethylamine, (R or S)-1-[4'-(2'- or 3'-chloro)pyridyl]-2-difluoroethylamine, (R or S)-1-[2'-(3'-, 4'-, 5'- or 6'-trifluoromethyl)pyridyl]-2-difluoroethylamine, (R or S)-1-[3'-(2'-, 4'-, 5'- or 6'-trifluoromethyl)pyridyl]-2-difluoroethylamine, (R or S)-1-[4'-(2'- or 3'-trifluoromethyl)pyridyl]-2-difluoroethylamine, (R or S)-1-[2'-(3'-, 4'-, 5'- or 6'-pentafluoroethyl)pyridyl]-2-difluoroethylamine, (R or S)-1-[3'-(2'-, 4'-, 5'- or 6'-pentafluoroethyl)pyridyl]-2-difluoroethylamine, (R or S)-1-[4'-(2'- or 3'-pentafluoroethyl)pyridyl]-2-difluoroethylamine, (R or S)-1-[2'-(3'-, 4'-, 5'- or 6'-methoxy)pyridyl]-2-difluoroethylamine, (R or S)-1-[3'-(2'-, 4'-, 5'- or 6'-methoxy)pyridyl]-2-difluoroethylamine, (R or S)-1-[4'-(2'- or 3'-methoxy)pyridyl]-2-difluoroethylamine, (R or S)-1-[2'-(3'-, 4'-, 5'- or 6'-ethoxy)pyridyl]-2-difluoroethylamine, (R or S)-1-[3'-(2'-, 4'-, 5'- or 6'-ethoxy)pyridyl]-2-difluoroethylamine, (R or S)-1-[4'-(2'- or 3'-ethoxy)pyridyl]-2-difluoroethylamine, (R or S)-1-[2'-(3'-, 4'-, 5'- or 6'-trifluoromethoxy)pyridyl]-2-difluoroethylamine, (R or S)-1-[3'-(2'-, 4'-, 5'- or 6'-trifluoromethoxy)pyridyl]-2-difluoroethylamine, (R or S)-1-[4'-(2'- or 3'-trifluoromethoxy)pyridyl]-2-difluoroethylamine, (R or S)-1-[2'-(3'-, 4'-, 5'- or 6'-pentafluoroethoxy)pyridyl]-2-difluoroethylamine, (R or S)-1-[3'-(2'-, 4'-, 5'- or 6'-pentafluoroethoxy)pyridyl]-2-difluoroethylamine, (R or S)-1-[4'-(2'- or 3'-pentafluoroethoxy)pyridyl]-2-difluoroethylamine, (R or S)-1-[2'-(3'-, 4'-, 5'- or 6'-methylamino)pyridyl]-2-difluoroethylamine, (R or S)-1-[3'-(2'-, 4'-, 5'- or 6'-methylamino)pyridyl]-2-difluoroethylamine, (R or S)-1-[4'-(2'- or 3'-methylamino)pyridyl]-2-difluoroethylamine, (R or S)-1-[2'-(3'-, 4'-, 5'- or 6'-dimethylamino)pyridyl]-2-difluoroethylamine, (R or S)-1-[3'-(2'-, 4'-, 5'- or 6'-dimethylamino)pyridyl]-2-difluoroethylamine, (R or S)-1-[4'-(2'- or 3'-dimethylamino)pyridyl]-2-difluoroethylamine, (R or S)-1-[2'-(3'-, 4'-, 5'- or 6'-methylthio)pyridyl]-2-difluoroethylamine, (R or S)-1-[3'-(2'-, 4'-, 5'- or 6'-methylthio)pyridyl]-2-difluoroethylamine, (R or S)-1-[4'-(2'- or 3'-methylthio)pyridyl]-2-difluoroethylamine, (R or S)-1-[2'-(3'-, 4'-, 5'- or 6'-ethylthio)pyridyl]-2-difluoroethylamine, (R or S)-1-[3'-(2'-, 4'-, 5'- or 6'-ethylthio)pyridyl]-2-difluoroethylamine, (R or S)-1-[4'-(2'- or 3'-ethylthio)pyridyl]-2-difluoroethylamine, (R or S)-1-(2'-thienyl)-2-monofluoroethylamine, (R or S)-1-(3'-thienyl)-2-monofluoroethylamine, (R or S)-1-[2'-(3'-, 4'- or 5'-methyl)thienyl]-2-monofluoroethylamine, (R or S)-1-[3'-(2'-, 4'- or 5'-methyl)thienyl]-2-monofluoroethylamine, (R or S)-1-[2'-(3'-, 4'- or 5'-ethyl)thienyl]-2-monofluoroethylamine, (R or S)-1-[3'-(2'-, 4'- or 5'-ethyl)thienyl]-2-monofluoroethylamine, (R or S)-1-[2'-(3'-, 4'- or 5'-fluoro)thienyl]-2-monofluoroethylamine, (R or S)-1-[3'-(2'-, 4'- or 5'-fluoro)thienyl]-2-monofluoroethylamine, (R or S)-1-[2'-(3'-, 4'- or 5'-chloro)thienyl]-2-monofluoroethylamine, (R or S)-1-[3'-(2'-, 4'- or 5'-chloro)thienyl]-2-monofluoroethylamine, (R or S)-1-[2'-(3'-, 4'- or 5'-fluoromethyl)thienyl]-2-monofluoroethylamine, (R or S)-1-[3'-(2'-, 4'- or 5'-trifluoromethyl)thienyl]-2-monofluoroethylamine, (R or S)-1-[2'-(3'-, 4'- or 5'-pentafluoroethyl)thienyl]-2-monofluoroethylamine, (R or S)-1-[3'-(2'-, 4'- or 5'-pentafluoroethyl)thienyl]-2-monofluoroethylamine, (R or S)-1-[2'-(3'-, 4'- or 5'-methoxy)thienyl]-2-monofluoroethylamine, (R or S)-1-[3'-(2'-, 4'- or 5'-methoxy)thienyl]-2-monofluoroethylamine, (R or S)-1-[2'-(3'-, 4'- or 5'-ethoxy)thienyl]-2-monofluoroethylamine, (R or S)-1-[3'-(2'-, 4'- or 5'-ethoxy)thienyl]-2-monofluoroethylamine, (R or S)-1-[2'-(3'-, 4'- or 5'-trifluoromethoxy)thienyl]-2-monofluoroethylamine, (R or S)-1-[3'-(2'-, 4'- or 5'-trifluoromethoxy)thienyl]-2-monofluoroethylamine, (R or S)-1-[2'-(3'-, 4'- or 5'-pentafluoroethoxy)thienyl]-2-monofluoroethylamine, (R or S)-1-[3'-(2'-, 4'- or 5'-pentafluoroethoxy)thienyl]-2-monofluoroethylamine, (R or S)-1-[2'-(3'-, 4'- or 5'-methylamino)thienyl]-2-monofluoroethylamine, (R or S)-1-[3'-(2'-, 4'- or 5'-methylamino)thienyl]-2-monofluoroethylamine, (R or S)-1-[2'-(3'-, 4'- or 5'-dimethylamino)thienyl]-2-monofluoroethylamine, (R or S)-1-[3'-(2'-, 4'- or 5'-dimethylamino)thienyl]-2-monofluoroethylamine, (R or S)-1-[2'-(3'-, 4'- or 5'-methylthio)thienyl]-2-monofluoroethylamine, (R or S)-1-[3'-(2'-, 4'- or 5'-methylthio)thienyl]-2-monofluoroethylamine, (R or S)-1-[2'-(3'-, 4'- or 5'-ethylthio)thienyl]-2-monofluoroethylamine, (R or S)-1-[3'-(2'-, 4'- or 5'-ethylthio)thienyl]-2-monofluoroethylamine, (R or S)-1-(2'-thienyl)-2-difluoroethylamine, (R or S)-1-(3'-thienyl)-2-difluoroethylamine, (R or S)-1-[2'-(3'-, 4'- or 5'-methyl)thienyl]-2-difluoroethylamine, (R or S)-1-[3'-(2'-, 4'- or 5'-methyl)thienyl]-2-difluoroethylamine, (R or S)-1-[2'-(3'-, 4'- or 5'-ethyl)thienyl]-2-difluoroethylamine, (R or S)-1-[3'-(2'-, 4'- or 5'-ethyl)thienyl]-2-difluoroethylamine, (R or S)-1-[2'-(3'-, 4'- or 5'-fluoro)thienyl]-2-difluoroethylamine, (R or S)-1-[3'-(2'-, 4'- or 5'-fluoro)thienyl]-2-difluoroethylamine, (R or S)-1-[2'-(3'-, 4'- or 5'-chloro)thienyl]-2-difluoroethylamine, (R or S)-1-[3'-(2'-, 4'- or 5'-chloro)thienyl]-2-difluoroethylamine, (R or S)-1-[2'-(3'-, 4'- or 5'-trifluoromethyl)thienyl]-2-difluoroethylamine, (R or S)-1-[3'-(2'-, 4'- or 5'-trifluoromethyl)thienyl]-2-difluoroethylamine, (R or S)-1-[2'-(3'-, 4'- or 5'-pentafluoroethyl)thienyl]-2-difluoroethylamine, (R or S)-1-[3'-(2'-, 4'- or 5'-pentafluoroethyl)thienyl]-2-difluoroethylamine, (R or S)-1-[2'-(3'-, 4'- or 5'-methoxy)thienyl]-2-difluoroethylamine, (R or S)-1-[3'-(2'-, 4'- or 5'-methoxy)thienyl]-2-difluoroethylamine, (R or S)-1-[2'-(3'-, 4'- or 5'-ethoxy)thienyl]-2-difluoroethylamine, (R or S)-1-[3'-(2'-, 4'- or 5'-ethoxy)thienyl]-2-difluoroethylamine, (R or S)-1-[2'-(3'-, 4'- or 5'-trifluoromethoxy)thienyl]-2-difluoroethylamine, (R or S)-1-[3'-(2'-, 4'- or 5'-fluoromethoxy)thienyl]-2-difluoroethylamine, (R or S)-1-[2'-(3'-, 4'- or 5'-pentafluoroethoxy)thienyl]-2-difluoroethylamine, (R or S)-1-[3'-(2'-, 4'- or 5'-pentafluoroethoxy)thienyl]-2-difluoroethylamine, (R or S)-1-[2'-(3'-, 4'- or 5'-methylamino)thienyl]-2-difluoroethylamine, (R or S)-1-[3'-(2'-, 4'- or 5'-methylamino)thienyl]-2-difluoroethylamine, (R or S)-1-[2'-(3'-, 4'- or 5'-dimethylamino)thienyl]-2-difluoroethylamine, (R or S)-1-[3'-(2'-, 4'- or 5'-dimethylamino)thienyl]-2-difluoroethylamine, (R or S)-1-[2'-(3'-, 4'- or 5'-methylthio)thienyl]-2-difluoroethylamine, (R or S)-1-[3'-(2'-, 4'- or 5'-methylthio)thienyl]-2-difluoroethylamine, (R or S)-1-[2'-(3'-, 4'- or 5'-ethylthio)thienyl]-2-difluoroethylamine and (R or S)-1-[3'-(2'-, 4'- or 5'-ethylthio)thienyl]-2-difluoroethylamine.

The present invention will be described below in more detail with reference to the following examples. It should be however noted that the following examples are only illustrative and not intended to limit the invention thereto.

EXAMPLE 1

Dehydration Condensation 1 (Monofluoro Compound)

To 39 ml of toluene was added 5.35 g (38.73 mmol, 1.00 eq) of monofluoromethyl phenyl ketone, 5.16 g (42.58 mmol, 1.10 eq) of (S)-1-phenylethylamine and 0.16 g (1.17 mmol, 0.03 eq) of zinc chloride, followed by stirring the resultant solution for 20 hours under heat reflux conditions while removing by-product water with the use of a Dean-Stark tube. The conversion rate of the reaction was determined by gas chromatography to be 99% or greater. The reaction terminated liquid was washed once with 30 ml of 1N aqueous sodium hydroxide solution and then washed six times with 40 ml of aqueous saturated ammonium chloride solution each. The recovered organic phase was dried with anhydrous sodium sulfate, concentrated under a reduced pressure and dried in a vacuum, thereby obtaining 8.91 g of a crude product of optically active imine represented by the following formula.

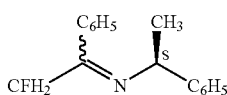

[Chem. 22]

The organic recovery of the crude product was 95%, and the gas-chromatographic purity of the crude product was 85.9%. Based on the $^1$H-NMR spectrum and $^{19}$F-NMR spectrum of the crude product, the stereochemistry of the double bond of the optically active imine was determined to be E- and Z-configurations with a E:Z ratio of 3:1. The $^1$H-NMR spectrum and $^{19}$F-NMR spectrum are indicated below.

$^1$H-NMR (standard substance: TMS, heavy solvent: CDCl$_3$), δ ppm: E configuration isomer/1.43 (d, 6.4 Hz, 3H), 4.56 (q, 6.4 Hz, 1H), 5.12 (d, 47.2 Hz, 2H), 7.00-7.60 (Ar—H, 10H); Z configuration isomer/1.58 (d, 6.6 Hz, 3H), 5.01 (q, 6.6 Hz, 1H), 5.31 (dd, 12.3 Hz, 46.1 Hz, 1H), 5.43 (dd, 12.3 Hz, 46.1 Hz, 1H), 7.00-7.60 (Are, 10H). $^{19}$F-NMR (standard substance: C$_6$F$_6$, heavy solvent: CDCl$_3$), δ ppm: E configuration isomer/206.98 (t, 47.2 Hz, 1F); Z configuration isomer/208.31 (t, 46.1 Hz, 1F).

EXAMPLE 2

Asymmetric Reduction and Salt Purification 1 (Monofluoro Compound)

To 37 ml of methanol was added 8.91 g (36.92 mmol, 1.00 eq) of the crude product of optically active imine prepared in Example 1, followed by adding 1.40 g (37.01 mmol, 1.00 eq) of sodium borohydride at −20° C. gradually over 30 minutes and stirring the resultant solution for 12 hours at room temperature. The conversion rate of the reaction was determined by gas chromatography to be 99% or greater. By adding 10 ml of 1N aqueous hydrochloride solution into the reaction-terminated liquid, an excess residue of sodium borohydride was decomposed. Further, the solution was made alkaline with 30 ml of 1N aqueous sodium hydroxide solution. The resultant solution was then extracted twice with 50 ml of toluene each. The recovered organic phase was washed once with 30 ml of saturated sodium chloride solution, dried with anhydrous sodium sulfate, concentrated under a reduced pressure and dried in a vacuum, thereby obtaining as a crude product 8.10 g of a diastereomeric mixture of optically active secondary amine represented by the following formula.

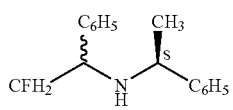

[Chem. 23]

The organic recovery of the crude product was 90%. The diastereomer excess of the crude product was determined by gas chromatography to be 20.7% d.e. (S—S configuration isomer>R—S configuration isomer). To a mixed solution of 50 ml of i-propanol and 120 ml of n-heptane were added 8.10 g (33.29 mmol, 1.00 eq) of the crude product of the diastereomeric mixture of optically active secondary amine and 6.33 g (33.28 mmol, 1.00 eq) of p-toluenesulfonic acid monohydrate. These added components were dissolved in the solution by heating. The temperature of the resultant solution was gradually decreased to room temperature over the night with stirring. The precipitated crystals were filtrated and dried in a vacuum, thereby obtaining 5.72 g of a crude product of optically active secondary amine p-toluenesulfonate salt (once-recrystallized product) represented by the following formula.

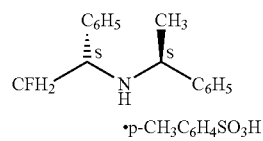

[Chem. 24]

The once-recrystallized product was converted to a free base by the after-mentioned technique. The diastereomer excess of the free base was determined to be 83.2% d.e. (S—S configuration isomer>R—S configuration isomer). Using a mixed solution of 70 ml of i-propanol and 50 ml of n-heptane, 5.72 g of the once-recrystallized product was purified by recrystallization in the same manner as above, thereby obtaining 4.90 g of optically active secondary amine p-toluenesulfonate salt (twice-recrystallized product). Then, 42 mg of the twice-recrystallized product was neutralized with 1 ml of 1N aqueous sodium hydroxide solution and extracted once with 2 ml of ethyl acetate. The recovered organic phase was dried with anhydrous sodium sulfate, concentrated under a reduced pressure and dried in a vacuum, thereby yielding a free base. The diastereomer excess of the free base was determined by gas chromatography to be 98.3% d.e. (S—S configuration isomer>R—S configuration isomer). The total recovery rate of the asymmetric reduction and salt purification was 32%. The $^1$H-NMR spectrum of the optically active secondary amine p-toluenesulfonate salt (S—S configuration isomer) is indicated below.

$^1$H-NMR (standard substance: TMS, heavy solvent: (CD$_3$)$_2$SO), δ ppm: 1.58 (d, 6.4 Hz, 3H), 2.28 (s, 3H), 4.22 (q, 6.4 Hz, 1H), 4.59 (dt, 17.5 Hz, 5.5 Hz, 1H), 4.83 (ddd, 5.5 Hz, 10.5 Hz, 46.1 Hz, 1H) 4.87 (ddd, 5.5 Hz, 10.5 Hz, 46.1 Hz, 1H), 7.11 (Ar—H, 2H), 7.37-7.54 (Ar—H, 12H), 9.54 (br, 1H), 9.77 (br, 1H).

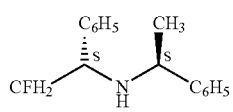

Further, the $^1$H-NMR spectrum and $^{19}$F-NMR spectrum of the optically active secondary amine (S—S configuration isomer, free base) represented by the above formula are indicated below.

$^1$H-NMR (standard substance: TMS, heavy solvent: CDCl$_3$), δ ppm: 1.37 (d, 6.7 Hz, 3H), 1.82 (br, 1H), 3.81 (q, 6.7 Hz, 1H), 4.04 (ddd, 4.4 Hz, 6.8 Hz, 16.5 Hz, 1H), 4.47 (ddd, 6.8 Hz, 9.0 Hz, 47.5 Hz, 1H), 4.53 (ddd, 4.4 Hz, 9.0 Hz, 47.5 Hz, 1H), 7.10-7.40 (Ar—H, 10H).

$^{19}$F-NMR (standard substance: C$_6$F$_6$, heavy solvent: CDCl$_3$), δ ppm: 206.59 (dt, 16.5 Hz, 47.5 Hz, 1F).

EXAMPLE 3

Hydrogenolysis 1 (Monofluoro Compound)

To 2 ml of methanol were added 415.5 mg (1.00 mmol, 1.00 eq) of the optically active secondary amine p-toluenesulfonate salt (twice-recrystallized product) prepared in Example 2 and 8.3 mg of 5 wt % Pd/C (50 wt % wet) (Pd: 0.21 mg, 0.0019 mmol, 0.0019 eq), followed by stirring the resultant solution at 60° C. for 12 hours under the hydrogen pressure of 0.5 MPa. The conversion rate of the reaction was determined by $^1$H-NMR to be 85.1%. Also, the regioselectivity of the hydrogenolysis was determined by $^1$H-NMR to be 94:6. The reaction-terminated liquid was filtered with a membrane filter. The resultant filtrate was concentrated under a reduced pressure and dried in a vacuum. The remaining solution was made alkaline with 5 ml of 1N aqueous sodium hydroxide solution and extracted once with 20 ml of toluene. The recovered organic phase was washed once with 7 ml of saturated sodium chloride solution, dried with anhydrous sodium sulfate, concentrated under a reduced pressure and dried in a vacuum, thereby obtaining 75.4 mg of a crude product of optically active 1-aryl-2-fluoro-substituted ethylamine represented by the following formula.

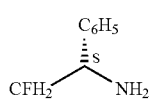

The organic recovery of the crude product was 54%. The crude product was unstable to gas chromatography. The optically active 1-aryl-2-fluoro-substituted ethylamine of the above formula was obtained with almost no loss of optical purity. The $^1$H-NMR spectrum and $^{19}$F-NMR spectrum are indicated below.

$^1$H-NMR (standard substance: TMS, heavy solvent: CDCl$_3$), δ ppm: 1.74 (br, 2H), 4.21-4.57 (complex peak pattern for 3H), 7.15-7.50 (Ar—H, 5H).

$^{19}$F-NMR (standard substance: C$_6$F$_6$, heavy solvent: CDCl$_3$), δ ppm: 208.36 (dt, 14.1 Hz, 47.3 Hz, 1F).

EXAMPLE 4

Dehydration Condensation 2 (Difluoro Compound)

To 39 ml of toluene was added 4.68 g (29.98 mmol, 1.00 eq) of difluoromethyl phenyl ketone, 4.00 g (33.01 mmol, 1.10 eq) of (S)-1-phenylethylamine and 0.12 g (0.88 mmol, 0.03 eq) of zinc chloride, followed by stirring the resultant solution for 44 hours under heat reflux conditions while removing by-product water through the use of a Dean-Stark tube. The conversion rate of the reaction was determined by gas chromatography to be 99% or greater. The reaction-terminated liquid was washed once with 10 ml of 5 wt % aqueous sodium hydroxide solution and then washed three times with 20 ml of aqueous saturated ammonium chloride solution each. The recovered organic phase was dried with anhydrous sodium sulfate, concentrated under a reduced pressure and dried in a vacuum, thereby obtaining 7.66 g of a crude product of optically active imine represented by the following formula.

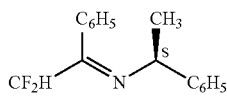

The organic recovery of the crude product was 99%, and the gas-chromatographic purity of the crude product was 99.2%. Based on the $^1$H-NMR spectrum and $^{19}$F-NMR spectrum of the crude product, the stereochemistry of the double bond of the optically active imine was determined to be E configuration with a E:Z ratio of 20:1. The $^1$H-NMR spectrum and $^{19}$F-NMR spectrum are indicated below.

$^1$H-NMR (standard substance: TMS, heavy solvent: CDCl$_3$), δ ppm: E configuration isomer/1.42 (d, 6.6 Hz, 3H), 4.58 (q, 6.6 Hz, 1H), 6.21 (t, 55.3 Hz, 1H), 7.10-7.55 (Ar—H, 10H).

$^{19}$F-NMR (standard substance: C$_6$F$_6$, heavy solvent: CDCl$_3$), δ ppm: E configuration isomer/43.94 (dd, 9.4 Hz, 55.3 Hz, 2F).

EXAMPLE 5

Asymmetric Reduction and Salt Purification 2 (Difluoro Compound)

To 30 ml of methanol was added 7.66 g (29.54 mmol, 1.00 eq) of the crude product of optically active imine prepared in Example 4, followed by adding 1.13 g (29.87 mmol, 1.01 eq) of sodium borohydride gradually over 30 minutes under cooling with ice and stirring the resultant solution for 3 days at room temperature. The conversion rate of the reaction was determined by gas chromatography to be 99% or greater. By adding 30 ml of 10 wt % aqueous hydrochloride solution into the reaction-terminated liquid, an excess residue of sodium borohydride was decomposed. Further, the solution was made alkaline with 30 ml of 1N aqueous sodium hydroxide solution. The resultant solution was then extracted three times with 50 ml of toluene each. The recovered organic phase was washed once with 50 ml of saturated sodium chloride solution, dried with anhydrous sodium sulfate, concentrated under a reduced pressure and dried in a vacuum, thereby obtaining as a crude product 5.68 g of a diastereomeric mixture of optically active secondary amine represented by the following formula.

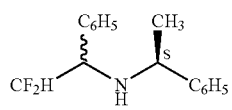

The organic recovery of the crude product was 74%, and the gas-chromatographic purity of the crude product was 81.8%. Further, the diastereomer excess of the crude product was determined by gas chromatography to be 58.0% d.e. (S—S configuration isomer>R—S configuration isomer).

To a mixed solution of 3 ml of i-propanol and 3 ml of n-heptane were added 1072.0 mg (at a gas-chromatographic purity of 81.8%, 3.36 mmol, 1.00 eq) of the crude product of the diastereomeric mixture of optically active secondary amine and 557.9 mg (3.36 mmol, 1.00 eq) of phthalic acid. These added components were dissolved in the solution by heating. The temperature of the resultant solution was gradually decreased to room temperature over 16 hours with stirring. The precipitated crystals were filtrated and dried in a vacuum, thereby obtaining 879.0 mg of a crude product of optically active secondary amine phthalate salt (once-recrystallized product) represented by the following formula.

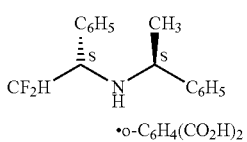

The recovery rate of the salt purification was 61%. The $^1$H-NMR spectrum of the optically active secondary amine phthalate (S—S configuration) is indicated below.

$^1$H-NMR (standard substance: TMS, heavy solvent: (CD$_3$)$_2$SO), δ ppm: 1.27 (d, 6.5 Hz, 3H), 3.33 (br, 3H), 3.79 (q, 6.5 Hz, 1H), 3.91 (dt, 4.5 Hz, 12.3 Hz, 1H), 6.15 (dt, 4.5 Hz, 56.0 Hz, 1H), 7.15-7.40 (Ar—H, 10H), 7.52-7.74 (Ar—H, 4H).

To 2.5 ml of 1N aqueous sodium hydroxide solution was added 427.4 mg of the once-recrystallized product, followed by stirring the resultant solution for 30 minutes at room temperature to neutralize the product with sodium hydroxide. The product was then extracted twice with 10 ml of toluene each. The recovered organic phase was washed once with 10 ml of water, dried with anhydrous sodium sulfate, concentrated under a reduced pressure and dried in a vacuum, thereby obtaining as a purified product 225.7 mg of optically active secondary amine (S—S configuration isomer, free base) represented by the following formula.

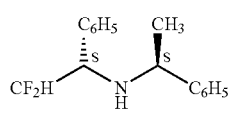

The recovery rate was 86%. The diastereomer excess of the free base was determined by gas chromatography to be 99.0% d.e. (S—S configuration isomer>R—S configuration isomer). The $^1$H-NMR spectrum of the optically active secondary amine (S—S configuration isomer, free base) is indicated below.

$^1$H-NMR (standard substance: TMS, heavy solvent: CDCl$_3$), δ ppm: 1.36 (d, 6.5 Hz, 3H), 1.80 (br, 1H), 3.88 (q, 6.5 Hz, 1H), 3.94 (dt, 4.4 Hz, 12.1 Hz, 1H), 5.88 (dt, 4.4 Hz, 56.5 Hz, 1H), 7.10-7.45 (Ar—H, 10H).

EXAMPLE 6

Hydrogenolysis 2 (Difluoro Compound)

To 2 ml of methanol were added 225.7 mg (0.86 mmol, 1.00 eq) of the optically active secondary amine (S—S configuration isomer, free base) prepared in Example 5 and 8.6 mg of 5 wt % Pd/C (50 wt % wet) (Pd: 0.22 mg, 0.0020 mmol, 0.0023 eq), followed by stirring the resultant solution at 60° C. for 24 hours under the hydrogen pressure of 0.5 MPa. The conversion rate of the reaction was determined by gas chromatography to be 99% or greater. The regioselectivity of the hydrogenolysis was determined by gas chromatography to be 99:1. The reaction-terminated liquid was filtered with a membrane filter. The resultant filtrate was concentrated under a reduced pressure and dried in a vacuum, thereby obtaining 132.5 mg of a crude product of optically active 1-aryl-2-fluoro-substituted ethylamine represented by the following formula.

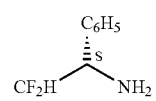

The organic recovery of the crude product was 84%. The optically active 1-aryl-2-fluorosubstituted ethylamine of the above formula was obtained with almost no loss of optical purity. The $^1$H-NMR spectrum and $^{19}$F-NMR spectrum are indicated below.

$^1$H-NMR (standard substance: TMS, heavy solvent: CDCl$_3$), δ ppm: 1.71 (br, 2H), 4.15 (ddd, 4.5 Hz, 9.6 Hz, 12.9 Hz, 1H), 5.74 (dt, 4.5 Hz, 56.5 Hz, 1H), 7.25-7.45 (Ar—H, 5H).

$^{19}$F-NMR (standard substance: C$_6$F$_6$, heavy solvent: CDCl$_3$), δ ppm: 34.52 (ddd, 12.9 Hz, 56.5 Hz, 277.6 Hz, 1F), 37.68 (ddd, 9.6 Hz, 56.5 Hz, 277.6 Hz, 1F).

The invention claimed is:

1. A method for producing an optically active 1-aryl-2-fluoro-substituted ethylamine compound of the formula [2] or a salt thereof by hydrogenolysis of an optically active secondary amine compound of the formula [1] or a salt thereof in the presence of a transition metal catalyst of Group VIII

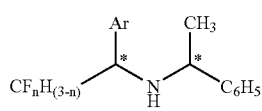

[where Ar represents an aryl group; n represents an integer of 1 or 2; and * represents an asymmetric carbon]

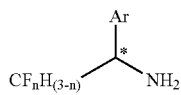
[2]

[where Ar represents an aryl group; n represents an integer of 1 or 2; and * represents an asymmetric carbon].

2. A method of producing an optically active 1-aryl-2-fluoro-substituted ethylamine compound of the formula [4] or a salt thereof by hydrogenolysis of an optically active secondary amine compound of the formula [3] or a salt thereof in the presence of a palladium catalyst

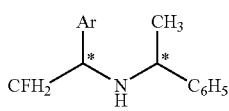
[3]

[where Ar represents an aryl group; and * represents an asymmetric carbon]

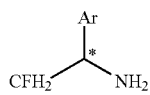
[4]

[where Ar represents an aryl group; and * represents an asymmetric carbon].

3. A method of producing an optically active 1-aryl-2-fluoro-substituted ethylamine compound of the formula [6] or a salt thereof by hydrogenolysis of an optically active secondary amine compound of the formula [5] or a salt thereof in the presence of a palladium catalyst

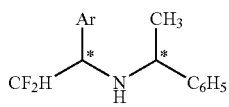
[5]

[where Ar represents an aryl group; and * represents an asymmetric carbon]

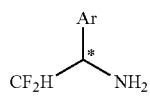
[6]

[where Ar represents an aryl group; and * represents an asymmetric carbon].

4. The method according to claim 1, wherein the optically active secondary amine compound of the formula [1] or the salt thereof is obtained by the steps of:

preparing an optically active imine of the formula [9] by dehydration condensation of a fluoro-substituted methyl aryl ketone of the formula [7] and an optically active 1-phenylethylamine of the formula [8] in the presence of an acid catalyst

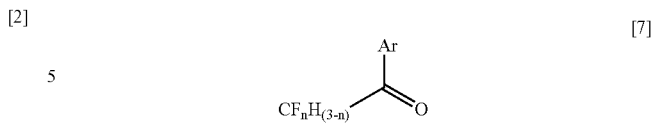
[7]

[where Ar represents an aryl group; and n represents an integer of 1 or 2]

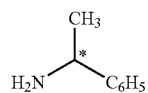
[8]

[where * represents an asymmetric carbon]

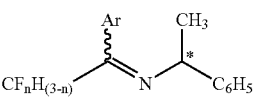
[9]

[where Ar represents an aryl group; n represents an integer of 1 or 2; * represents an asymmetric carbon; and the wavy line represents E configuration or Z configuration];

preparing an optically active secondary amine of the formula [10] in the form of a mixture of diastereomers by asymmetric reduction of the optically active imine

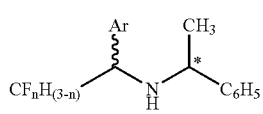
[10]

[where Ar represents an aryl group; n represents an integer of 1 or 2; * represents an asymmetric carbon; and the wavy line represents a mixture of diastereomers];

deriving a salt from the mixture of diastereomers of the optically active secondary amine; and purifying the salt by recrystallization.

5. The method according to claim 2, wherein the optically active secondary amine of the formula [3] or the salt thereof is obtained by the steps of:

preparing an optically active imine of the formula [12] by dehydration condensation of a fluoro-substituted methyl aryl ketone of the formula [11] and an optically active 1-phenylethylamine of the formula [8] in the presence of an acid catalyst

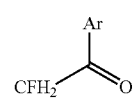
[11]

[where Ar represents an aryl group]

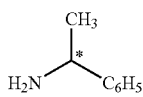
[8]

[where * represents an asymmetric carbon]

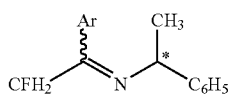
[12]

[where Ar represents an aryl group; * represents an asymmetric carbon; and the wavy line represents E configuration or Z configuration];

preparing an optically active secondary amine of the formula [13] in the form of a mixture of diastereomers by asymmetric reduction of the optically active imine with a hydride reducing agent

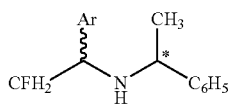
[13]

[where Ar represents an aryl group; * represents an asymmetric carbon; and the wavy line represents a mixture of diastereomers];

deriving a salt from the mixture of diastereomers of the optically active secondary amine; and purifying the salt by recrystallization.

6. The method according to claim 3, wherein the optically active secondary amine of the formula [5] or the salt thereof is obtained by the steps of:

preparing an optically active imine of the formula [15] by dehydration condensation of a fluoro-substituted methyl aryl ketone of the formula [14] and an optically active 1-phenylethylamine of the formula [8] in the presence of an acid catalyst

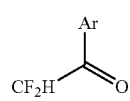
[14]

[where Ar represents an aryl group]

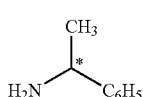
[8]

[where * represents an asymmetric carbon]

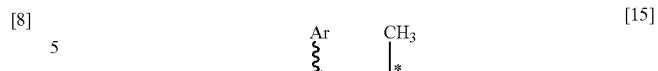
[15]

[where Ar represents an aryl group; * represents an asymmetric carbon; and the wavy line represents E configuration or Z configuration];

preparing an optically active secondary amine of the formula [16] in the form of a mixture of diastereomers by asymmetric reduction of the optically active imine with a hydride reducing agent

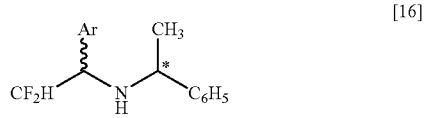
[16]

[where Ar represents an aryl group; * represents an asymmetric carbon; and the wavy line represents a mixture of diastereomers];

deriving a salt from the mixture of diastereomers of the optically active secondary amine; and purifying the salt by recrystallization.

7. An optically active imine of the formula [9]

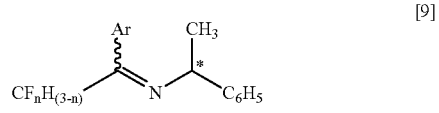
[9]

[where Ar represents an aryl group; n represents an integer of 1 or 2; * represents an asymmetric carbon; and the wave line represents E configuration or Z configuration].

8. An optically active secondary amine compound of the formula [1] or a salt thereof

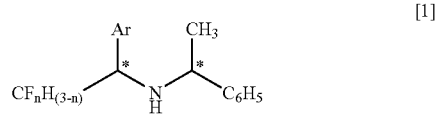
[1]

[where Ar represents an aryl group; n represents an integer of 1 or 2; and * represents an asymmetric carbon].

9. An optically active imine of the formula [12]

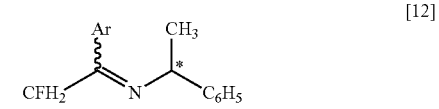
[12]

[where Ar represents an aryl group; * represents an asymmetric carbon; and the wave line represents E configuration or Z configuration].

10. An optically active secondary amine compound of the formula [3] or a salt thereof

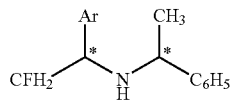
[3]

[where Ar represents an aryl group; and * represents an asymmetric carbon].

11. An optically active imine of the formula [15]

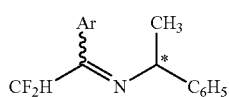
[15]

[where Ar represents an aryl group; * represents an asymmetric carbon; and the wave line represents E configuration or Z configuration].

12. An optically active secondary amine compound of the formula [5] or a salt thereof

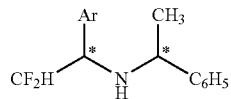
[5]

[where Ar represents an aryl group; and * represents an asymmetric carbon].

13. An optically active 1-aryl-2-fluoro-substituted ethylamine compound of the formula [2] or a salt thereof

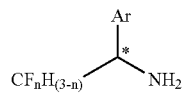
[2]

[where Ar represents an aryl group; n represents an integer of 1 or 2; and * represents an asymmetric carbon].

14. An optically active 1-aryl-2-fluoro-substituted ethylamine compound of the formula [4] or a salt thereof

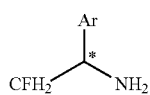
[4]

[where Ar represents an aryl group; and * represents an asymmetric carbon].

15. An optically active 1-aryl-2-fluoro-substituted ethylamine compound of the formula [6] or a salt thereof

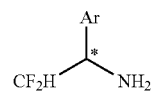
[6]

[where Ar represents an aryl group; and * represents an asymmetric carbon].

16. A method for producing a salt of an optically active 1-aryl-2-fluoro-substituted ethylamine compound of the formula [2] by hydrogenolysis of an optically active secondary amine compound of the formula [1] in the presence of an acid and a transition metal catalyst of Group VIII

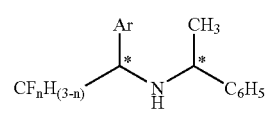
[1]

[wherein Ar represents an aryl group; n represents an integer of 1 or 2; and * represents an asymmetric carbon]

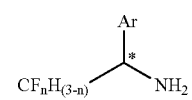
[2]

[wherein Ar represents an aryl group; n represents an integer of 1 or; and * represents an asymmetric carbon].

17. The method according to claim 16, wherein the acid is p-toluenesulfonic acid.

18. The method according to claim 16, wherein the amount of said acid is 0.8 mol or greater relative to 1 mol of the optically active secondary amine compound of the formula [1].

19. A method of producing an optically active 1-aryl-2-fluoro-substituted ethylamine compound of the formula [2], comprising:
preparing a salt of the optically active 1-aryl-2-fluoro-substituted ethylamine compound by hydrogenolysis of an optically active secondary amine compound of the formula [1] in the presence of an acid and a transition ametal catalyst of Group VIII

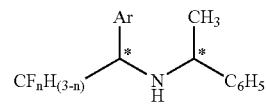
[1]

[wherein Ar represents an aryl group; n represents an integer of 1 or 2; and * represents an asymmetric carbon]

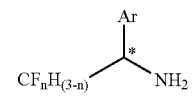
[2]

[wherein Ar represents an aryl group; n represents an integer of 1 or; and * represents an asymmetric carbon]; and
neutralizing the salt of the optically active 1-aryl-2-fluoro-substituted ethylamine compound with an aqueous solution of inorganic base.

20. A method of producing a salt of an optically active 1-aryl-2- fluoro-substituted ethylamine compound of the formula [2]

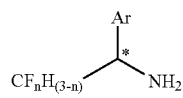

[2]

[wherein Ar represents an aryl group; n represents an integer of 1 or; and * represents an asymmetric carbon], the method comprising:
preparing an optically active imine of the formula [9] by dehydration condensation of a fluoro-substituted methyl aryl ketone of the formula [7] and an optically active 1-phenylethylamine of the formula [8] in the presence of an acid catalyst

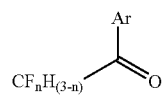

[7]

[where Ar represents an aryl group; and n represents an integer of 1 or 2]

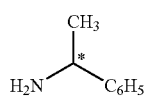

[8]

[where * represents an asymmetric carbon]

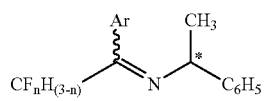

[9]

[where Ar represents an aryl group; n represents an integer of 1 or 2; * represents an asymmetric carbon; and the wavy line represents E configuration or Z configuration];
preparing a disastereomeric mixture of an optically active secondary amine of the formula [10] by asymmetric reduction of the optically active imine of the formula [9]

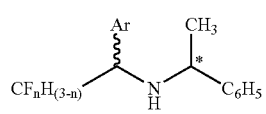

[10]

[where Ar represents an aryl group; n represents an integer of 1 or 2; * represents an asymmetric carbon; and the wavy line represents a mixture of diastereomers];

deriving a salt from an optically active secondary amine compound of the formula [1] from the diasteremeric mixture of the optically active secondary amine of the formula [10];

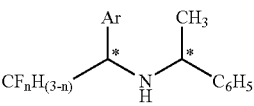

[1]

[where Ar represents an aryl group; n represents an integer of 1 or 2; and * represents an asymmetric carbon];
purifying the salt of the optically active secondary amine compound of the formula [1] by recrystallization; and
conducting hydrogenolysis of the purified salt of the optically active secondary amine compound of the formula [1] in the presence of a transition metal catalyst of Group VIII.

21. A method of producing an optically active 1-aryl-2-fluoro- substituted ethylamine compound of the formula [2]

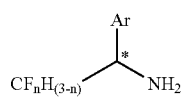

[2]

[wherein Ar represents an aryl group; n represents an integer of 1 or; and * represents an asymmetric carbon], the method comprising:
preparing an optically active imine of the formula [9] by dehydration condensation of a fluoro- substituted methyl aryl ketone of the formula [7] and an optically active 1-phenylethylamine of the formula [8] in the presence of an acid catalyst

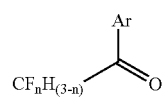

[7]

[where Ar represents an aryl group; and n represents an integer of 1 or 2]

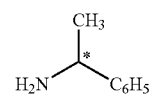

[8]

[where * represents an asymmetric carbon]

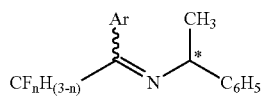

[9]

[where Ar represents an aryl group; n represents an integer of 1 or 2; * represents an asymmetric carbon; and the wavy line represents E configuration or Z configuration];

preparing a diastereomeric mixture of an optically active secondary amine of the formula [10] by asymmetric reduction of the optically active imine of the formula [9]

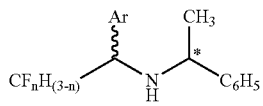

[10]

[where Ar represents an aryl group; n represents an integer of 1 or 2; * represents an asymmetric carbon; and the wavy line represents a mixture of diastereomers];

deriving a salt from an optically active secondary amine compound of the formula [1] from the diastereomeric mixture of the optically active secondary amine of the formula [10];

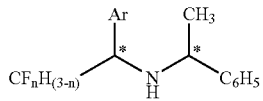

[1]

[where Ar represents an aryl group; n represents an integer of 1 or 2; and * represents an asymmetric carbon];

purifying the salt of the optically active secondary amine compound of the formula [1] by recrystallization;

preparing the salt of the optically active 1-aryl-2-fluoro-substituted ethylamine compound of the formula [2] by hydrogenolysis of the purified salt of the optically active secondary amine compound of the formula [1] in the presence of a transition metal catalyst of Group VIII; and neutralizing the salt of the optically active 1-aryl-2-fluoro-substituted ethylamine compound of the formula [2] with an aqueous solution of inorganic base.

* * * * *